US009012208B2

United States Patent
Selden et al.

(10) Patent No.: US 9,012,208 B2
(45) Date of Patent: *Apr. 21, 2015

(54) NUCLEIC ACID PURIFICATION

(75) Inventors: Richard F. Selden, Lincoln, MA (US); Eugene Tan, Arlington, MA (US)

(73) Assignee: NetBio, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/699,564

(22) Filed: Feb. 3, 2010

(65) Prior Publication Data

US 2010/0285578 A1 Nov. 11, 2010

Related U.S. Application Data

(60) Provisional application No. 61/206,690, filed on Feb. 3, 2009, provisional application No. 61/207,017, filed on Feb. 6, 2009.

(51) Int. Cl.
*C12M 3/00* (2006.01)
*C12M 1/34* (2006.01)
(Continued)

(52) U.S. Cl.
CPC ..... *B01L 3/502715* (2013.01); *B01L 3/502753* (2013.01); *B01L 3/5029* (2013.01); *B01L 3/50825* (2013.01); *B01L 7/52* (2013.01); *B01L 2200/027* (2013.01); *B01L 2200/16* (2013.01); *B01L 2300/0816* (2013.01); *B01L 2300/0867* (2013.01); *B01L 2300/087* (2013.01);
(Continued)

(58) Field of Classification Search
USPC .............. 435/7.21, 91.2, 287.1–287.3, 288.5, 435/288.7, 303.1, 91.1, 6.15–6.19, 288.6, 435/259, 325; 422/68.1
See application file for complete search history.

(56) References Cited

U.S. PATENT DOCUMENTS

| 4,713,219 A | 12/1987 | Gerken et al. |
| 4,753,536 A | 6/1988 | Spehar et al. |

(Continued)

FOREIGN PATENT DOCUMENTS

| WO | 02/18902 | 3/2002 |
| WO | 2007149791 | 12/2007 |

(Continued)

OTHER PUBLICATIONS

In re Donohue, 766 F.2d 531, 226 USPQ 619 (Fed. Cir. 1985).*

(Continued)

*Primary Examiner* — Michael Marcheschi
*Assistant Examiner* — Shanta G Doe
(74) *Attorney, Agent, or Firm* — Proskauer Rose LLP

(57) ABSTRACT

A self-contained apparatus for isolating nucleic acid, cell lysates and cell suspensions from unprocessed samples apparatus, to be used with an instrument, includes at least one input, and: (i) a macrofluidic component, including a chamber for receiving an unprocessed sample from a collection device and at least one filled liquid purification reagent storage reservoir; and (ii) a microfluidic component in communication with the macrofluidic component through at least one microfluidic element, the microfluidic component further comprising at least one nucleic acid purification matrix; and (iii) at least one interface port to a drive mechanism on the instrument for driving said liquid purification reagent, through the microfluidic element and the nucleic acid purification matrix, wherein the only inputs to the apparatus are through the chamber and the interface port to the drive mechanism.

11 Claims, 16 Drawing Sheets

(51) Int. Cl.
*B01L 3/00* (2006.01)
*C12N 15/10* (2006.01)
*B01L 7/00* (2006.01)

(52) U.S. Cl.
CPC .. *B01L2300/0887* (2013.01); *B01L 2400/0487* (2013.01); *C12N 15/1003* (2013.01)

(56) References Cited

U.S. PATENT DOCUMENTS

| | | | |
|---|---|---|---|
| 6,340,589 | B1 | 1/2002 | Turner et al. |
| 6,914,137 | B2 | 7/2005 | Baker |
| 6,958,392 | B2 | 10/2005 | Fomoskain et al. |
| 7,547,510 | B2 | 6/2009 | Daniel et al. |
| 8,018,593 | B2 | 9/2011 | Tan et al. |
| 2001/0027745 | A1* | 10/2001 | Weigl et al. .......... 117/206 |
| 2002/0019060 | A1* | 2/2002 | Petersen et al. ....... 436/514 |
| 2002/0197631 | A1* | 12/2002 | Lawrence et al. ......... 435/6 |
| 2004/0086870 | A1* | 5/2004 | Tyvoll et al. ............. 435/6 |
| 2006/0213964 | A1* | 9/2006 | Excoffier et al. ....... 235/375 |
| 2007/0092901 | A1 | 4/2007 | Ligler et al. |
| 2007/0184547 | A1* | 8/2007 | Handique et al. ..... 435/288.5 |
| 2008/0014576 | A1 | 1/2008 | Jovanovich et al. |
| 2009/0253181 | A1* | 10/2009 | Vangbo et al. ......... 435/91.1 |

FOREIGN PATENT DOCUMENTS

| | | |
|---|---|---|
| WO | 2008/124064 | 10/2008 |
| WO | 2008/124116 | 10/2008 |

OTHER PUBLICATIONS

In re Gleave, 560 F.3d 1331, 1335-36 (Fed. Cir. 2009).*
Nickolaus Blin & Darrel W. Stafford, "A general method for isolation of high molecular weight DNA from eukaryotes," Nucleic Acids Research, Sep. 1976, pp. 2303-2308; vol. 3, No. 9.
Brent Johnson, "Breaking Up Isn't Hard to Do: A cacophony of sonicators, cell bombs, and grinders," The Scientist, Nov. 9, 1998, p. 23, vol. 12, Issue 22.
"Phusion Blood Direct PCR Kit," Finnzymes, Espoon, Finland, 4 pages, Version 1.2, Jun. 2009.
A. Manz et al., "Minaturized Total Chemical Analysis Systems: a Novel Concept for Chemical Sensing," Sensors and Acutators, B1, 1990, pp. 244-248, Elsevier Sequoia, The Netherlands.
David Erickson & Dongqing Li, "Integrated microfluidic devices," Analytica Chimica Acta 507, 2003, pp. 11-26, Elsevier.
Benjamin J. Hindson et al., "Autonomous Detection of Aerosolized Biological Agents by Multiplexed Immunoassay with Polymerase Chain Reaction Confirmation," Analytical Chemistry, Jan. 1, 2005, pp. 284-289, vol. 77, No. 1, American Chemical Society.
Donald M. Wallace, "Precipitation of Nucleic Acids," Methods in Enzymology, 1987, pp. 41-48, vol. 152, Academic Press, Inc.
Bert Vogelstein & David Gillespie, "Preparative and analytical purification of DNA from agarose," Proceedings of the National Academy of Sciences of the USA, Feb. 1979, pp. 615-619, vol. 76, No. 2.
Peter H. Von Hippel & Kwok-Ying Wong, "Neutral Salts: The Generality of Their Effects on the Stability of Macromolecular Conformations," Science, New Series, vol. 145, No. 3632, Aug. 7, 1964, pp. 577-580, American Association for the Advancement of Science.
John M. Chirgwin et al., "Isolation of Biologically Active Ribonucleic Acid from Sources Enriched in Ribonuclease," Biochemistry, 1979, pp. 5294-5299, vol. 18, No. 24, American Chemical Society.
R. Boom et al., "Rapid and Simple Method for Purification of Nucleic Acids," Journal of Clinical Microbiology, Mar. 1990, pp. 495-503, vol. 28, No. 3, American Society for Microbiology.
P. Sean Walsh et al., "Chelex 100 as a Medium for Simple Extraction of DNA for PCR-Based Typing from Forensic Material," BioTechniques, Apr. 1991, pp. 506-513, vol. 10, No. 4, Eaton Publishing Co., Natick, MA.

Maria Fernanda Lazzarino et al., "DNA Recovery from Semen Swabs with the DNA IQ System," Forensic Science Communications, Jan. 2008, vol. 10, No. 1, Federal Bureau of Investigation.
Jessica V. Norris et al., "Expedited, Chemically Enhanced Sperm Cell Recovery from Cotton Swabs for Rape Kit Analysis," Journal of Forensic Science, Jul. 2007, pp. 800-805, vol. 52, No. 4, American Academy of Forensic Science.
Jessica C. Voorhees et al., "Enhanced Elution of Sperm from Cotton Swabs Via Enzymatic Digestion for Rape Kit Analysis," Journal of Forensic Science, May 2006, pp. 574-579, vol. 51, No. 3, American Academy of Forensic Science.
Carl K. Fredrickson & Z. Hugh Fan, "Macro-to-micro interfaces for microfluidic devices," Lab Chip, 2004, pp. 526-533, vol. 4, No. 6, The Royal Society of Chemistry.
Kelley A. Wolfe et al., "Toward a microchip-based solid-phase extraction method for isolation of nucleic acids," Electrophoresis, 2002, pp. 727-733, vol. 23, Wiley-VCH Verlag GmbH, Weinhelm, Germany.
Jain Wen et al., "DNA Extraction Using a Tetramethyl Orthosilicate-Grafted Photopolymerized Monolithic Solid Phase," Analytical Chemistry, Mar. 1, 2006, pp. 1673-1681, vol. 78, No. 5, American Chemical Society.
Christopher J. Easley et al., "A fully integrated microfluidic genetic analysis system with sample-in-answer-out capability," Proceedings of the National Academy of Sciences of the USA, Dec. 19, 2006, pp. 19272-19277, vol. 103, No. 51.
Kristin A. Hagan et al., "Microchip-Based Solid-Phase Purification of RNA from Biological Samples," Analytical Chemistry, Nov. 15, 2008, pp. 8453-8460, vol. 80, No. 22, American Chemical Society.
Holger Becker & Laurie E. Locascio, "Polymer microfluidic devices," Talanta, 2002, pp. 267-287, vol. 56, No. 2, Elsevier Science.
Larisa Martynova et al., "Fabrication of Plastic Microfluid Channels by Imprinting Methods," Analytical Chemistry, Dec. 1, 1997, pp. 4783-4789, vol. 69, No. 23, American Chemical Society.
Eric T. Lagally et al., "Fully integrated PCR-capillary electrophoresis microsystem for DNA analysis," Lab in a Chip, 2001, pp. 102-107, vol. 1, No. 2, The Royal Society of Chemistry.
Stephanie H.I. Yeung, "Rapid and High-Throughput Forensic Short Tandem Repeat Typing Using a 96-Lane Microfabricated Capillary Array Electrophoresis Microdevice," Journal of Forensic Science, Jul. 2006, pp. 740-747, vol. 51, No. 4, American Academy of Forensic Science.
Robin Hui Liu et al., "Self-Contained, Fully Integrated Biochip for Sample Preparation, Polymerase Chain Reaction Amplification, and DNA Microarray Detection," Analytical Chemistry, Apr. 1, 2004, pp. 1824-1831, vol. 76, No. 7, American Chemical Society.
Peng Liu & Richard A. Mathies, "Integrated microfluidic systems for high-performance genetic analysis," Trends in Biotechnology, 2009, pp. 572-581, vol. 27, No. 10, Elsevier.
Chia-Wen Tsao & Don L. Devoe, "Bonding of thermoplastic polymer microfluidics," Microfluid Nanofluid, 2009, pp. 1-16, vol. 6, Springer.
Peter Leemans et al., "Evaluation of methodology for the isolation and analysis of LCN-DNA before and after dactyloscopic enhancement of fingerprints," International Congress Series 1288, 2005, pp. 583-585, Elsevier.
Henry C. Lee & Carll Ladd, "Preservation and Collection of Biological Evidence," Croation Medical Journal, 2001, pp. 225-228, vol. 42, No. 3.
Chunsun Zhang et al., "Micropumps, microvalues, and micromixers within PCR microfluidic chips: Advances and trends," Biotechnology Advances 25, 2007, pp. 483-514, Elsevier.
Frank B. Cogswell et al., "Host DNA Can Interfere with Detection of *Borrelia burgdorferi* in Skin Biopsy Specimens by PCR," Journal of Clinical Microbiology, Apr. 1996, pp. 980-982, vol. 34, No. 4, American Society for Microbiology.

* cited by examiner

NUCLEIC ACID PURIFICATION

CROSS-REFERENCE TO RELATED APPLICATIONS

This application claims the benefit of the filing dates of U.S. Provisional Application Ser. No. 61/206,690, filed Feb. 3, 2009; and No. 61/207,017, filed Feb. 6, 2009; each of which is hereby incorporated by reference in its entirety.

STATEMENT OF GOVERNMENT INTEREST

This application was supported by Grant Number 2007-DN-BS-K184 awarded by the National Institutes of Justice, Office of Justice Programs, US Department of Justice and a contract from MIT Lincoln Laboratory entitled "Field-Deployable Accelerated Nuclear DNA Equipment" awarded on Sep. 30, 2009.

BACKGROUND OF THE INVENTION

A. The Unmet Need—Unprocessed Clinical and Forensic Samples

From the first isolation of nucleic acids by Miescher and Altmann in the second half of the nineteenth century (Miescher, Friedrich (1871) "Ueber die chemische Zusammensetzung der Eiterzellen," in F. Miescher. Die Histochemischen and physiologischen Arbeiten Vol. 2:3-23) to the most sophisticated molecular biological techniques available today, the process of DNA extraction has been streamlined substantially. Nevertheless, there is a pressing need in the clinical, biothreat detection, and forensics communities for sensitive, robust, and reliable integrated methods of DNA purification that are rapid, cost-effective, and neither labor- nor space-intensive. In particular, there is an unmet need for methods and devices that can rapidly purify nucleic acids from unprocessed clinical or forensic field samples without any manual handling or processing.

Ideally, novel methods for nucleic acid purification are needed to address the numerous and varied existing and emerging markets for delivering genomic information, particularly the delivery of genomic information in the field, and for point-of-care and near point-of-care applications. For example, in the field of human identification, there is an unmet need in the forensic community to be able to generate a DNA fingerprint rapidly, whether in the laboratory or in the field (e.g. at borders, ports of entry, the battlefield, and military checkpoints).

Similarly, in order to protect civilian and military populations, it is critical to improve the identification of environmental biothreats. More rapid, more sensitive, more specific, and more detailed identification will allow improved strategic and tactical responses by civilian and military authorities, and more effective remediation activities. The rapid application of nucleic acid analysis technologies including nucleic acid amplification, hybridization, and sequencing can provide critical information in this regard.

Furthermore, the ability to rapidly diagnose clinical infections (whether caused by biothreats or conventional pathogens) would have a profound impact on society. For example, drawing a blood sample from a septic patient and determining both the identity of the pathogen or pathogens as well as their antibiotic resistance profiles based on nucleic acid analyses within an hour or less would allow specific antimicrobial therapy to begin immediately (the analogous situation for viral diagnostics and drug resistance profiles is also critically important). The ability to rapidly generate nucleic acid analytic information from clinical samples would also have substantial impact on the diagnosis and treatment of a wide range of diseases ranging from cancers to immune system disorders; essentially every category of diseases would be impacted. The same approach could also be applied to pharmacogenomics, the use of genetic information to predict the suitability of a given pharmacologic intervention.

B. Prior Art Approaches to DNA Purification

The basic approach to extraction and purification of nuclear DNA from mammalian cells was developed over three decades ago (N. Blin, D. W. Stafford (1976). A general method for isolation of high molecular weight DNA from eukaryotes. *Nucleic Acids Res.* 3(9): 2303-8) and has two major steps: the lysis of the cell types of interest and the purification of DNA from other cellular components in solution (particularly proteins) and cellular and tissue debris. Cell lysis and (when appropriate) DNA solubilization can be accomplished by mechanical (reviewed in J. Brent (1998). Breaking Up Isn't Hard To Do: A cacophony of sonicators, cell bombs and grinders" *The Scientist* 12(22):23) and non-mechanical techniques. Simple mechanical approaches include the use of a blenders and homogenization by forcing cells through restrictive openings. Sonication is based on the exposure of cells to high-frequency sound waves, and bead approaches are based on exposing cells to violent mixing in the presence of various beads.

Chemical disruption of cells is an alternative to mechanical disruption. Detergents are important chemical lytic agents that act by disrupting lipid bilayers. Additional properties of detergents may allow protein structure to be maintained (e.g. zwitterionic and nonionic detergents) or disrupted (ionic detergents). Sodium dodecyl sulfate (SDS), an ionic detergent, is commonly used in forensic DNA extraction protocols due in part to its ability to solubilize macromolecules and denature proteins within the cell (J. L. Haines et al (2005) Current Protocols in Human Genetics Vol. 2, (2005 John Wiley and Sons, Inc. Pub.). Proteinase K is often used in tandem with detergent-based (e.g. SDS, Tween-20, Triton X-100) lysis protocols. Another form of detergent lysis is based on FTA paper (L. A. Burgoyne (1997) Convenient DNA Collection and Processing: Disposable Toothbrushes and FTA Paper as a Non-threatening Buccal-Cell Collection Kit Compatible with Automatable DNA Processing, 8th International Symposium on Human Identification, Sep. 17-20, 1997 Orlando, Fla.; G. M. Fomovskaia et al., U.S. Pat. No. 6,958,392). This is a cellulose filter impregnated with a weak base, an anionic detergent, a chelating agent, and preservatives.

In the case of a clinical or environmental sample, a critical first step towards nucleic acid analysis is the isolation or purification of some or all of the nucleic acid present in the sample. The biological material in the sample may be lysed and nucleic acids within the lysate may be purified prior to further analysis. Alternatively, nucleic acids contained within the lysate may be analyzed directly (e.g. Phusion Blood Direct PCR kit (Finnzymes, Espoo, FN) and Daniel et al., U.S. Pat. No. 7,547,510).

As those skilled in the art will recognize, purifying nucleic acids from unprocessed clinical, environmental, or forensic samples requires the automation of pre-processing steps suited to the particular field sample under investigation. The diversity of sample types, sample volumes, sampling technologies, sample collection devices, sample processing requirements, and the complexities inherent in resolving field samples has created an unmet need for robust methods and devices for purifying nucleic acids from such diverse samples.

C. Microfluidic Approaches to Purification from Clinical and Environmental Samples The field of microfluidics offers a potential solution to the unmet need for methods and devices capable of isolating nucleic acids from unprocessed clinical, environmental, and forensic samples. Microfluidics is based on the manipulation of small fluid volumes of microliters or less and emerged as a hybrid of molecular biology and microelectronics in the early 1990's (See Manz et al. *Sens. Actuators* B1:244-248 (1990)). A major focus in microfluidics is to integrate multiple components to develop a system with sample-in, results-out functionality (reviewed in Erickson et al., *Anal. Chimica Acta* 507: 11-26 (2004)).

Some progress using this approach has been made with regard to environmental detection of biothreats. The automated pathogen detection system (Hindon et al., *Anal. Chem.* 77:284-289 (2005)) collects air samples and performs microfluidic DNA extraction and real-time PCR capable of detecting *B. anthracis* and *Y. pestis* (detection limits were between $10^3$-$10^7$ organisms per mL of concentrated sample). The Cepheid (Sunnyvale, Calif.) GeneXpert system also collects air samples and performs integrated *B. anthracis* spore lysis (by microsonication), DNA extraction, and real-time PCR (detection limits were 68 cfu (equivalent to 148 spores) per mL concentrated sample for Ames spores and $10^2$-$10^3$ cfu per mL concentrated sample for Sterne spores). Despite these advances, there is no available system or device capable of purifying unprocessed nucleic acids from clinical or environmental samples (or from environmental samples collected manually) without human intervention. Indeed, all of the available technologies rely on manual processing of some or all of the steps.

D. DNA Purification from Forensic Samples

One of the earliest DNA purification methods for forensic samples was the use of phenol/chloroform extraction (D. M. Wallace (1987) Large and small scale phenol extractions. *Methods Enzymol.* 152:33-41; Maniatis, T. et al., "Purification of Nucleic Acids" in Molecular Cloning: A Laboratory Manual, 3rd Ed. Cold Spring Harbor Laboratory, Cold Spring Harbor, N.Y.). In this method, most protein moves to the organic phase or the organic-aqueous interface, and solubilized DNA remains in the aqueous phase. The DNA-containing phase can be subjected to ethanol precipitation, and DNA isolated following a series of centrifugation and wash steps. In forensic practice, DNA is often recovered from the aqueous phase with centrifugal dialysis devices, such as the Microcon columns (Millipore Corporation, Billerica, Mass.). The advantage of the organic extraction approach is that it yields high quality DNA preparations (with relatively low amounts of protein and relatively low degradation) and remains one of the most reliable methods available today. The major disadvantages are that the procedure is time- and labor-intensive, requires cumbersome equipment, and is relatively difficult to adapt to high-throughput settings.

Accordingly, the forensic community has moved to a series of purification technologies that are simpler to use, many of which serve as the basis of commercially available kits. There are an enormous number of approaches to nucleic acid purification, several of which are summarized as follows:

Silica Matrices/Chaotropic Agents.

The use of silica beads for DNA isolation has been a standard technique for over a quarter century, with the initial protocols based on the binding of DNA to silica in the presence of chaotropic agents such as sodium iodide (B. Vogelstein et al., (1979) "Preparative and analytical purification of DNA from agarose," *Proc Nat Acad Sci USA* 76(2):615-9). Many years earlier, guanidinium salts had been found to be potent destabilizers of macromolecules (von Hippel P. H. et al., (1964) "Neutral Salts: The Generality of Their Effects on the Stability of Macromolecular Conformations." *Science* 145:577-580). Certain guanidinium salts also have the advantage of deactivating nucleases (Chirgwin J. M. et al., (1979) "Isolation of biologically active ribonucleic acid from sources enriched in ribonuclease," *Biochemistry* 18(24):5294-9). These observations were synthesized by Boom (Boom, R. et al., (1990) "Rapid and Simple method for purification of nucleic acids," *J Clin Microbiol.* 28(3):495-503), who, in effect, used two related properties of guanidinium salts. The first, the ability of the salts to lyse cells, and the second, the ability of the salts to enhance DNA binding to silica particles, have led to a number of lysis/purification approaches widely utilized in forensics laboratories today (e.g. DNAIQ Systems, Promega, Madison, Wis.). An alternative to silica beads is the use of silica membranes (QIAamp, Qiagen Hilden, Del.). In addition, the silica beads themselves may be modified to further enhance DNA binding.

Silica Matrices/Non-Chaotropic Agents.

Silica matrices can also be utilized in the absence of chaotropes. One approach is to modify silica beads such that they have a net positive charge at a given pH and are capable of binding DNA (Baker, M. J., U.S. Pat. No. 6,914,137). The modification contains an ionizable group, such that the DNA binding is reversed at a higher pH (when the ionizable group is neutral or negatively charged), sometimes at elevated temperature. As wide swings in pH can damage DNA, a critical feature of this approach is to choose a modification that allows reversible binding of DNA within a relatively narrow pH range. A widely used approach of this type is based on the ChargeSwitch bead (Life Technologies, Inc. Carlsbad, Calif.).

Magnetic Beads.

Although DNA binding properties are determined primarily by the surface structure of a given bead, the use of magnetic beads has become increasingly important in DNA purification protocols. These particles are generally paramagnetic; they are not themselves magnetic but form dipoles when exposed to a magnetic field. The utility of these beads relates to their ease of handling and adaptation to automated systems. For example, beads can be readily removed from a suspension in the presence of a magnet, allowing them to be washed and transported efficiently. Two commonly used magnetic beads are the ChargeSwitch and DNAIQ beads described above.

Ion Exchange.

Ion exchange allows DNA molecules to reversibly bind to an immobile bead. The bead generally consists of a porous organic or inorganic polymer with charged sites that allow one ion to be replaced by another at a given ionic strength. In practice, a solution containing DNA and other macromolecules is exposed to the ion exchange resin. The negatively charged DNA (due to its phosphate backbone) binds relatively strongly to the resin at a given salt concentration or pH. Protein, carbohydrate, and other impurities bind relatively weakly (if at all) and are washed from the beads (e.g. in a column format or by centrifugation). Purified DNA can then be eluted in a high ionic strength buffer. A commercially available anion exchange resin used today is based on DEAE-modified silica beads (Genomic-tip, Qiagen).

Chelex.

Chelex-100 (Bio-Rad, Hercules, Calif.). is a modified resin that efficiently binds multivalent metal cations. As such cations are required for enzymes that degrade DNA and themselves inhibit PCR enzymes, this method is representative of those that essentially avoid a DNA purification step (Walsh P. S. et al., Chelex 100 as a medium for simple extraction of DNA for PCR-based typing from forensic material. *Biotechniques* 10(4):506-13).

When using cotton swabs to collect material, there can be problems removing biological material from the cotton matrix; as the cotton swab dries after collection, the biological material can adhere to the swab. For example, due to the saccharic composition of the spermatocyte membrane, spermatocytes stick to solid supports, especially cotton (Lazzarino, M. F. et al, (2008) DNA Recovery from Semen Swabs with the DNA IQ System. *Forensic Science Communications* 10(1)). In order to release the maximum amount of material from the swabs, a variety of buffers have been tested and compared to the standard differential extraction buffer. Use of detergents such as 1-2% sodium dodecyl sulfate (SDS) has shown to increase sperm cell recovery (Norris, J. V. et al., (2007) "Expedited, chemically enhanced sperm cell recovery from cotton swabs for rape kit analysis." J Forensic Sci 52(4): 800-5). Also, the addition of low amounts of cellulase has shown to release more epithelial and sperm cells from the cotton swab matrix than buffer elution alone (Voorhees, J. C. et al., (2006). "Enhanced elution of sperm from cotton swabs via enzymatic digestion for rape kit analysis." J Forensic Sci 51(3): 574-9).

There can be many challenges to obtaining forensic short tandem repeat (STR) profiles from biological materials including low quantity or quality of DNA. Low copy number samples (containing less than 50-100 picograms of DNA) as well as low quality, degraded samples require highly efficient collection, extraction, and amplification procedures. These samples are seen in a variety of forensic evidence including touch evidence and aged samples. Amplification kits such as the Life Technologies Minifiler™ have smaller amplicon sizes which have shown to increase the ability to obtain STR profiles from these difficult samples.

PCR inhibitors are another challenge and must be eliminated before downstream applications can be performed. Common inhibitors are indigo dyes from denim, heme from blood, humic acid found in plants and soil, and collagen found in various tissues. The majority of these inhibitors are effectively eliminated using silica based DNA extraction methods or additional purification with charge or size exclusion columns. The presence of inhibitors can be detected by performing PCR with internal positive controls. If present, some inhibitors can be neutralized by various treatments including sodium hydroxide washes or further purification with Millipore Microcon YM® columns.

The need to reconcile the "real world" requirements of sample collection with the microfluidic requirements of a fully integrated microfluidic DNA processing biochip can be referred to as the "macro-to-micro interface" or the "world-to-chip interface" (Fredrickson, C. and Fan, Z. (2004) "Macro-to-micro interfaces for microfluidic devices," Lab Chip 4(6): 526-33). Much of the reported research on addressing this interface is focused on resolving the mismatch between the macrofluidic and microfluidic volumetric requirements, but little or no research concerning the reconciling of specific forensic sampling requirements and formats with microfluidic devices has been reported.

The (non-forensic) volumetric mismatch has been commercially addressed by Agilent (Santa Clara, Calif.) in the Bioanalyzer 2100 by the use of a capillary to aspirate samples from a microtiter plate to a chip for enzyme assays (Lin 2003). Similarly, Gyros (Uppsala, SE) has developed a capillary dispenser for a LabCD system where samples are aspirated from a well plate into a dispensing nozzle and then directed upwards onto a rotating device (Jesson 2003). These devices, however, do not address the format incompatibility of collected forensic samples—particularly on the commonly used collection devices based on swabs.

E. Partially Automated DNA Purification

A variety of laboratory instruments have been developed for the partially automated purification of nucleic acids. For example, the Maxwell 16 instrument (Promega) is designed to purify nucleic acids from forensic samples. To purify DNA from a buccal swab, the operator performs a number of steps including cutting the cotton collection portion in half, placing it into a 1.5 mL centrifuge tube, preparing and adding lysis reagents, incubating the sample in a heat block, vortexing the tube, transferring the reagents and swab sample to a spin basket, and centrifuging the basket. Next, a plunger is placed into the Maxwell cartridge, the sample is pipetted into the cartridge, and the cartridge is placed into the instrument for nucleic acid purification.

The iPrep instrument (Life Technologies) is also used for the processing of forensic and clinical samples to purify nucleic acids. For example, the tip of a buccal swab is placed into a 1.5 mL centrifuge tube and subjected to a series of manual steps similar to those required for the Maxwell 16. After manual sample preparation, the crude lysate is transferred to a 1 mL elution tube for processing within the instrument. The Qiagen EZ1, BioRobot M48, and Qiacube systems (Qiagen) partially automate nucleic acid purification. Buccal swabs are collected, allowed to dry for two hours, and manually processed essentially as with the instruments described above. Innuprep (analytikJena, Itzehoe, Del.), LabTurbo (Taigen, Taipei, TW), Xiril 150 (Xiril AG, Hombrechtikon, CH), and Quickgene (FujiFilm Corp., Tokyo, JP) systems are partially automated instruments requiring substantial user manipulation and intervention. U.S. Patent App. Pub. No. 20080003564 (Chen et al) describes a macrofluidic sample processing tube that accepts a swab and transports reagents mechanically using macrofluidic features and flexible tubing. US Patent App. Pub. No. 20070092901 (Ligler, F. et al.) have described a system that accepts liquid biological samples for semi-automated nucleic acid purification.

Several groups including those of Landers (Wolfe, K. A. et al., (2002) Toward a microchip-based solid phase extraction method for isolation of nucleic acids. *Electrophoresis* 23 (5):727-33; Wen, J. et al., (2006) DNA extraction using a tetramethyl orthosilicate-grafted photopolymerized monolithic solid phase. *Anal Chem.* 78(5):1673-81; Easley, C. J. et al., (2006) A fully integrated microfluidic genetic analysis system with sample-in-answer-out capability. *Proc Natl Acad Sci USA* 103(51):19272-7); Hagan K. A. et al. (2008) Microchip-based solid-phase purification of RNA from biological samples, *Anal Chem* 80:8453-60), Locascio (Becker, H. et al., (2002) Polymer microfluidic devices Talanta 56(2):267-287; Martynova, L. et al., (1997) Fabrication of plastic microfluid channels by imprinting methods. *Anal Chem.* 69(23):4783-9.), Mathies (Lagally, E. T. et al., (2001) Fully integrated PCR-capillary electrophoresis microsystem for DNA analysis. *Lab Chip* 1(2):102-7: Yeung, S. H., et al., (2006) Rapid and high-throughput forensic short tandem repeat typing using a 96-lane microfabricated capillary array electrophoresis microdevice. *J Forensics Sci.* 51(4):740-7), and others (Liu R. H. et al., (2004) "Self-contained, fully integrated biochip for sample preparation, polymerase chain reaction, amplification, and DNA microarray detection Anal Chem 76(7):1824-31) have been working on microfluidics for DNA purification and analysis (reviewed in Liu, P. and Mathies, R. A., (2009), "Integrated microfluidic systems for high-performance genetic analysis." *Trends in Biotechnology* 27(10): 572-81). Easley has demonstrated DNA isolation from 750 nanoliters of whole blood and 1 microliter of nasal aspirate using a guanidinium lysis/silica bead purification protocol (Easley, C. J. et al., *Proc Natl Acad Sci* supra). The whole blood sample contained approximately 2.5 million bacteria (*Bacillus anthracis*) per mL 1500-2000 cfu in the 750 nL sample), a concentration too high to be relevant for clinical diagnostics. U.S. Patent App. US2008/0014576 A1 describes nucleic acid purification modules that accept samples for purification in solutions, beads, colloids, or multiple-phase solutions and may be integrated with downstream preparation devices such as thermal cyclers and separation instruments.

SUMMARY OF THE INVENTION

The inventions of this disclosure comprise apparatus, methods and instruments for isolating nucleic acid, cell lysates and cell suspensions from unprocessed samples. In one invention, the apparatus comprises a self-contained apparatus for isolating nucleic acid from an unprocessed sample, said apparatus to be used with an instrument, said apparatus comprising, at least one input, and:
(i) a macrofluidic component, comprising a chamber for receiving said unprocessed sample from a collection device and at least one filled liquid purification reagent storage reservoir; and
(ii) a microfluidic component in communication with said macrofluidic component via at least one microfluidic element, said microfluidic component further comprising;
at least one nucleic acid purification matrix
(iii) a drive mechanism on said instrument for driving said liquid purification reagent, through said microfluidic element and said nucleic acid purification matrix, wherein the only inputs to said apparatus are via said chamber and said drive mechanism.

In another invention, the apparatus comprises a self-contained apparatus for isolating nucleic acid from an unprocessed sample, said apparatus to be used with an instrument, said apparatus comprising, at least one input, and:
(i) a macrofluidic component comprising:
a chamber for receiving said unprocessed sample from a collection device;
at least two pre-filled lysis reagent storage reservoirs;
a pre-filled wash reagent storage reservoir; and
a pre-filled elution reagent storage reservoir; and
(ii) a microfluidic component in communication with said macrofluidic component via at least one microfluidic element, said microfluidic component further comprising; at least one nucleic acid purification matrix;
(iii) a drive mechanism on said instrument for driving said first and second lysis reagents, said wash reagent, and said elution reagent and sequentially through said microfluidic element and said nucleic acid purification matrix, wherein the only inputs to said apparatus are via said chamber and said drive mechanism.

In related inventions, the claimed apparatus may have collection devices and/or chambers are labeled, said labels comprising and a bar code or RFID. In other related inventions, the drive mechanisms may be pneumatic, mechanical, magnetic, or fluidic. In still other related inventions the unprocessed sample comprises: (i) a nasal swab, nasopharyngeal swab, buccal swab, oral fluid swab, stool swab, tonsil swab, vaginal swab, cervical swab, blood swab, wound swab, or tube containing blood, sputum, purulent material, or aspirates; (ii) a forensic swab, cutting, adhesive tape lift, or card; or (iii) an environmental air filter, water filter, or swab.

In other related inventions the purification matrix of the claimed apparatus comprises silica membranes, silica beads, silica magnetic beads, ion exchange resins, or ion exchange beads. In still other related inventions the microfluidic component of the claimed apparatus comprises channels, reservoirs, active valves, passive valves, pneumatically actuated valves, reaction chambers, mixing chambers, venting elements, access holes, pumps, metering elements, mixing elements, heating elements, magnetic elements, reaction chambers, filtration elements, purification elements, drive lines, and actuation lines.

Another invention of this disclosure is a method for purifying nucleic acids from an unprocessed sample comprising,
providing a sample comprising nucleic acids to the chamber of a claimed apparatus;
driving at least a portion of a first lysis reagent from said first lysis reagent chamber into the chamber to provide a first mixture;
driving at least a portion of a second lysis reagent from said second lysis reagent chamber into the chamber to provide a second mixture;
driving at least a portion of the said second mixture through the purification membrane to provide a filtrate and a retentate, wherein the retentate comprises at least a portion of the nucleic acids;
driving at least a portion of the wash reagent through the purification membrane to provide a washed retentate and a waste;
optionally drying the washed retentate; and
collecting at least a portion of the nucleic acids from the washed retentate by driving at least a portion of an elution reagent from the elution reagent chamber through the purification matrix.

Yet another invention of this disclosure is a method for purifying nucleic acids from an unprocessed sample comprising,
providing a sample comprising nucleic acids to the chamber of a claimed apparatus;
driving at least a portion of a first lysis reagent from said first lysis reagent chamber into the chamber to provide a first mixture;
bubbling a gas through the first mixture to provide a stirred first mixture
driving at least a portion of a second lysis reagent from said second lysis reagent chamber into the chamber to provide a second mixture; and
driving at least a portion of the stirred first mixture through the purification matrix to provide a filtrate and a retentate, wherein the retentate comprises at least a portion of the nucleic acids;
driving at least a portion of the wash reagent through the purification matrix to provide a washed retentate and a waste;
optionally drying the washed retentate;
driving at least a portion of an elution reagent from the elution reagent chamber through the purification matrix to provide an eluted nucleic acid solution; and bubbling a gas through the eluted nucleic acid solution to provide a homogenized eluted nucleic acid solution.

Still another invention of this disclosure is a method for purifying nucleic acids from pathogens in whole blood comprising, providing a sample comprising anticoagulated whole blood and pathogens in a blood collection tube to the sample collection chamber of a claimed apparatus;

driving at least a portion of the blood through a leukocyte retention filter to provide a reduced-leukocyte filtrate;

driving at least a portion of a leukocyte wash reagent through the leukocyte retention filter to provide a washed reduced-leukocyte filtrate;

driving at least a portion of the a reduced-leukocyte filtrate through a pathogen capture membrane driving at least a portion of the pathogen resuspension solution across the capture membrane to provide a concentrated pathogen suspension driving at least a portion of the concentrated pathogen suspension into a first lysis reagent chamber containing said first lysis reagent to provide a first mixture;

driving at least a portion of a second lysis reagent from said second lysis reagent chamber into the first lysate reagent chamber to provide a second mixture; driving at least a portion of the said second mixture through the purification membrane to provide a filtrate and a retentate, wherein the retentate comprises at least a portion of the nucleic acids;

driving at least a portion of the wash reagent through the purification membrane to provide a washed retentate and a waste;

optionally drying the washed retentate; and collecting at least a portion of the nucleic acids from the washed retentate by driving at least a portion of an elution reagent from the elution reagent chamber through the purification matrix.

Another invention of this disclosure is a method for purifying nucleic acids from pathogens in whole blood comprising, providing a sample comprising anticoagulated whole blood and pathogens in a blood collection tube to the sample collection chamber of a claimed apparatus;

driving at least a portion of the blood through a leukocyte retention filter to provide a reduced-leukocyte filtrate;

driving at least a portion of a leukocyte wash reagent through the leukocyte retention filter to provide a washed reduced-leukocyte filtrate;

driving at least a portion of the leukocyte resuspension solution across the retention filter to provide a concentrated leukocyte suspension;

driving at least a portion of the concentrated leukocyte suspension into a first lysis reagent chamber containing said first lysis reagent to provide a first mixture;

driving at least a portion of a second lysis reagent from said second lysis reagent chamber into the first lysate reagent chamber to provide a second mixture; driving at least a portion of the said second mixture through the purification membrane to provide a filtrate and a retentate, wherein the retentate comprises at least a portion of the nucleic acids;

driving at least a portion of the wash reagent through the purification membrane to provide a washed retentate;

optionally drying the washed retentate; and collecting at least a portion of the nucleic acids from the washed retentate by driving at least a portion of an elution reagent from the elution reagent chamber through the purification matrix.

In a related invention the method additionally comprises, driving a leukocyte lysis solution into the concentrated leukocyte suspension to provide a differentially lysed suspension; driving at least a portion of the differentially lysed suspension through a pathogen retention filter; driving at least a portion of the retention filter wash reagent through the pathogen retention filter to provide a washed pathogen retentate; and resuspending, lysing, and purifying nucleic acids from the pathogen retentate.

Another invention of this disclosure is a self-contained apparatus for generating cell lysate from an unprocessed sample, said apparatus to be used with an instrument, said apparatus comprising at least one input, and:

(i) a macrofluidic component, comprising: a chamber for receiving said unprocessed sample from a collection device, and at least one filled reagent storage reservoir; and (ii) a microfluidic component in communication with said macrofluidic component via at least one microfluidic element; and (iii) a drive mechanism on said instrument for driving said reagent, through said microfluidic element, wherein the only inputs to said apparatus are via said chamber and said drive mechanism.

Yet another invention is a self-contained apparatus for lysing cells from an unprocessed sample, said apparatus to be used with an instrument, said apparatus comprising at least one input, and:

(i) a macrofluidic component, comprising a chamber for receiving said unprocessed sample from a collection device and at least one pre-filled lysis storage reservoir; and (ii) a microfluidic component in communication with said macrofluidic component via at least one microfluidic element; and (iii) a drive mechanism on said instrument for driving reagent in said storage reservoir, through said microfluidic element, wherein the only inputs to said apparatus are via said chamber and said drive mechanism.

In a related inventive method for lysing cells from a sample comprising using the apparatus, comprising at least one input, and: providing a sample comprising cells to a chamber; introducing said lysis reagent into the chamber to provide a mixture; bubbling a gas through the mixture to provide a stirred mixture; wherein the stirred mixture comprises lysed cells.

Still another invention is a self-contained apparatus for generating a suspension of cells from an unprocessed sample, said apparatus to be used with an instrument, said apparatus comprising at least one input, and:

(i) a macrofluidic component, comprising: a chamber for receiving said unprocessed sample from a collection device, and at least one filled reagent storage reservoir storing a substantially isotonic reagent; and (ii) a microfluidic component in communication with said macrofluidic component via at least one microfluidic element; and (iii) a drive mechanism on said instrument for driving said reagent, through said microfluidic element, wherein the only inputs to said apparatus are via said chamber and said drive mechanism.

In another invention, the instruments which comprise the claimed inventive apparatus also perform at least one of thermal cycling, capillary electrophoresis, microfluidic electrophoresis, nucleic acid fragment sizing, short tandem repeat (STR), Y-STR, and mini-STR, single nucleotide polymorphism, PCR, highly multiplexed PCR, Real-time-PCR, Reverse Transcription PCR, sequencing, hybridization, microarray, VNTR, immunoassays, mass spectroscopy and RFLP analyses.

In still another invention, the apparatus of the invention can be placed into or interface with another instrument that performs at least one of thermal cycling, capillary electrophoresis, microfluidic electrophoresis, nucleic acid fragment sizing, short tandem repeat (STR), Y-STR, and mini-STR, single nucleotide polymorphism, PCR, highly multiplexed PCR, Real-time-PCR, Reverse Transcription PCR, sequencing, hybridization, microarray, VNTR, immunoassays, mass spectroscopy and RFLP analyses.

It also is an invention of this disclosure that the claimed apparatus and instruments are ruggedized to withstand transport and extremes of at least one of temperature, humidity, and airborne particulates.

DETAILED DESCRIPTION OF THE INVENTION

Figure 1:
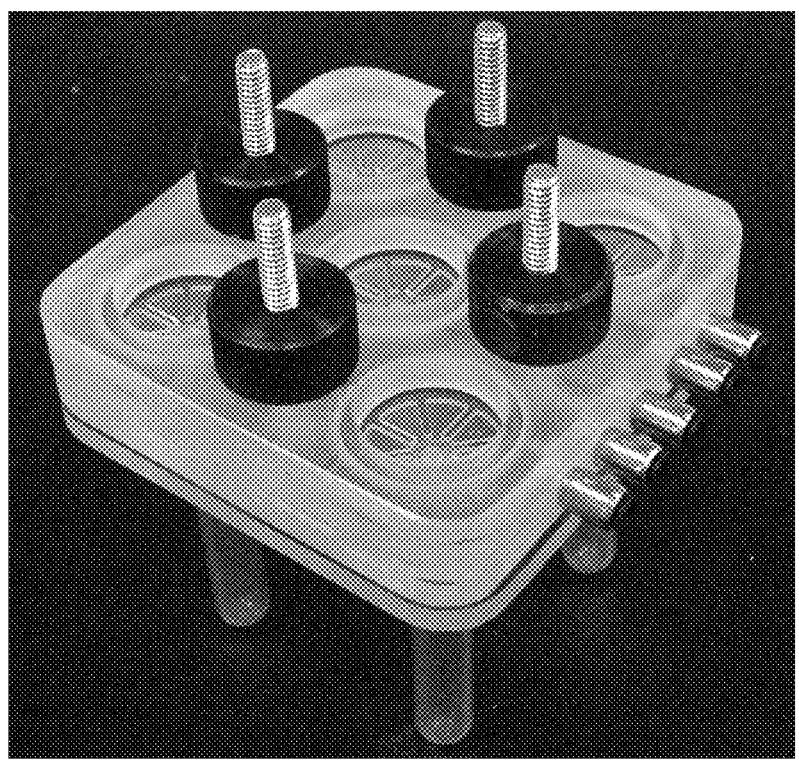
FIG. 1 depicts an apparatus suitable for biothreat detection from a blood sample.

The invention provides a series of apparatus, instrumentation, and methods that can be used to provide rapid, efficient purification of nucleic acids from a variety of biological sample types. As illustrated in the examples herein, nucleic acid can be purified based on devices comprising both macrofluidic and microfluidic features and accompanying instrumentation. In general, the macrofluidic component of the apparatus of this invention comprises chambers (including sample, reagent storage reservoir, reaction, holding, homogenization, and waste chambers) with aggregate volume of 1-1000 mL or greater and individual volumes of 1 mL and greater. Particularly preferred are aggregate volumes in the range of 1-250 mL. The macrofluidic component may also optionally comprise chambers with volumes of 20-1000 µL. The microfluidic component comprises microfluidic elements with microliter and nanoliter volumes. It is preferred that the microfluidic elements have individual volumes in the range of 0.1-1000 µL and particularly preferred that the individual elements have volumes of 0.1 to 100 µL.

The teachings of the invention can be applied to nucleic acid purification such that the nucleic acid product can be removed and analyzed separately or the nucleic acid can be transferred directly to analytic modules in an integrated instrument. Types of analysis and approaches to such integration include those described in Tan et al., Integrated Nucleic Acid Analysis, PCT/US08/04462, which is herein fully incorporated by reference.

The apparatus and instrumentation of the invention allow nucleic acid to be purified from unprocessed biological samples. Unprocessed biological samples are those that are collected by an individual and then inserted into the sample receiving chamber of the apparatus with no intermediate processing steps (although the sample collection device may be labeled and/or stored prior to processing). The operator need only collect or otherwise obtain the sample, insert the sample into the apparatus, insert the apparatus into the instrument (not necessary if the apparatus was previously placed in the instrument), and press a start button. No processing, manipulation, or modification of the sample is required prior to insertion in the apparatus—the operator does not have to cut a swab, open a blood tube, collect a tissues or biologic fluid, transfer a sample to another holder, or expose the sample to a reagent or a condition (e.g. heat, cold, vibration). Accordingly, the operator need not have extensive training in the biological sciences or laboratory techniques.

The apparatus of the invention are self-contained in that the only inputs to the apparatus are via the sample receiving chamber and the drive mechanism. As all required reagents are present within the apparatus in pre-filled reagent storage reservoirs, the operator is not required to add process reagents to the apparatus. The fact that the apparatus contains all reagents on-board is an important factor in ease of operation. Similarly, as the instrument contains no purification process reagents, the operator need not add reagents to the instrument. The self-contained nature of the apparatus minimizes operating procedures, maintenance procedures, and operator requirements. Taken together, the self-contained apparatus and the use of unprocessed samples dramatically simplifies the process of nucleic acid purification. Another advantage of the self-contained apparatus of the invention is that this format reduces both the possibility of sample contamination as well as operator exposure to sample, reagents, and process waste.

Furthermore, the apparatus and instrumentation of the invention are designed to be operable outside of conventional laboratory environments. Depending upon the application, they can be ruggedized to withstand transport and extremes of temperature, humidity, and airborne particulates. Use of the invention by non-technical operators in offices, out of doors, in the battlefield, in airports, at borders and ports, and at the point-of-care will allow much broader application of genetic technology in society. The use of unprocessed samples in a self-contained apparatus further supports the broad application of the methods of the invention.

In practice, biological samples are collected using a myriad of collection devices, all of which can be used with the apparatus of the invention. The collection devices will generally be commercially available but can also be specifically designed and manufactured for a given application. For clinical samples, a variety of commercial swab types are available including nasal, nasopharyngeal, buccal, oral fluid, stool, tonsil, vaginal, cervical, and wound swabs. The dimensions and materials of the sample collection devices vary, and the devices may contain specialized handles, caps, scores to facilitate and direct breakage, and collection matrices. Blood samples are collected in a wide variety of commercially available tubes of varying volumes, some of which contain additives (including anticoagulants such as heparin, citrate, and EDTA), a vacuum to facilitate sample entry, a stopper to facilitate needle insertion, and coverings to protect the operator from exposure to the sample. Tissue and bodily fluids (e.g. sputum, purulent material, aspirates) are also collected in tubes, generally distinct from blood tubes. These clinical sample collection devices are generally sent to sophisticated hospital or commercial clinical laboratories for testing (although certain testing such as the evaluation of throat/tonsillar swabs for rapid streptococcal tests can be performed at the point of care). Environmental samples may be present as filters or filter cartridges (e.g. from air breathers, aerosols or water filtration devices), swabs, powders, or fluids.

Collection of biological evidence from crime scenes is a process that gathers a number of cells from a variety of surfaces, preserves the collected cells to minimize molecular degradation, and allows release of the collected material for downstream processing. Blood, semen, epithelial cells, urine, saliva, stool, various tissues, and bone can be associated with the crime scene and require careful and effective collection (Lee, H. C. et al., (1998) "Forensic applications of DNA typing: part 2: collection and preservation of DNA evidence." *Am J Forensic Med Pathol* 19(1): 10-8.

A common collection technique for forensic evidence is performed using a cotton swab. A single swab is taken from an area or a wet-dry double swab technique can be used. The double swab technique may be the most prevalent and a number of different fluids including water, buffered saline, or lysis buffers can be used to moisten the first swab (Leemans, P. 2006. "Evaluation and methodology for the isolation and analysis of LCN-DNA before and after dactyloscopic enhancement of fingerprints." *Int Congress Ser* 1288: 583-5). This technique allows for dried samples to become re-hydrated, with the majority of material collected on the first swab and the dry second swab collecting the remainder of the sample. In addition to cotton, the swab collection matrix can be comprised of various materials such as natural fiber (cotton) and synthetic matrices (modified cellulose, foam, Nylon, Polyester and Rayon). Swabs are commercially available from Bode (Lorton Va.), Puritan (Guilford, Me.), Fitzco (Spring Park, Minn.), Boca (Coral Springs, Fla.), Copan (Murrieta, Calif.) and Starplex (Etobicoke, ON, Canada). Swabbing can also be performed using gauze-like materials, disposable brushes, or commercially available biological sampling kits (Lauk, C. and Schaaf, J. 2007. "A new approach for the extraction of DNA from postage stamps" *Forensic Science Communications* 9(1)).

Another forensic collection technique involves taking cuttings of the area of interest such as a biological fluid from clothing; however this destroys the integrity of the evidence. Adhesive tape lifts are also used on a variety of surfaces to collect trace evidence that may contain human DNA. Cards such as FTA cards (Whatman plc, Kent, UK) are also used to collect samples.

Biological evidence from an individual that is present in person is often collected using buccal swabs. A widely used commercial buccal swab is the SecurSwab (The Bode Technology Group, Lorton, Va.). Buccal samples are collected by instructing the subject or operator to place the swab into the mouth on the inner cheek surface and to move the swab up and down one or more times.

After the unprocessed samples of the invention are collected, if they are not processed immediately they are sometimes allowed to dry to prevent fungal or bacterial growth. Evidentiary samples are generally not immediately sealed in plastic, which can result in microbial growth and cause degradation of the DNA. Typically, swabs or cuttings are placed in breathable containers made of paper or cardboard. Storing collected evidence in cool, dry environments also minimizes sample deterioration (Lee, H. C. and Ladd, C. (2001) "Preservation and Collection of Biological Evidence" *Croat Med J* 42(3): 225-8). To be truly useful to the forensic community, nucleic acid purification apparatus, instrumentation, and methods should be able to obtain highly purified nucleic acids from commercially available collection devices and be compatible with accepted forensic collection and analysis protocols.

Regardless of the type of sample, the sample receiving chamber of the apparatus and the cover (if present) are designed to accept and fit snugly with the sample collection device. In the case of samples such as cloth or adhesive tape (e.g. sample collection devices that have no handle or cap), following their placement into the chamber, a snug-fitting cap is placed on the cover to close the chamber. Depending on application, the sample collection device can be locked (reversibly or irreversibly) into the apparatus. Furthermore, the device and apparatus can form a seal (air- and water-tight); in this case, a vent or vent membrane may be placed to allow fluid flow into the chamber. Unless otherwise specified, the chambers of the apparatus that receive fluid from elsewhere on the apparatus must contain vents or vent membranes to allow for air to escape during chamber filling.

The apparatus of the invention comprise a macrofluidic component and a microfluidic component in communication with one another. The macrofluidic component comprises a sample chamber for receiving a biological sample from a sample collection device, and other chambers that may include reservoirs for purification reagents, holding chambers, homogenization chambers, metering chambers, reaction chambers, mixing chambers, and waste chambers. The microfluidic component comprises a chamber comprising a nucleic acid purification media and at least one microfluidic feature and one pneumatic drive-line. The macrofluidic chambers are in communication with microfluidic features and the macrofluidic chambers are in communication with each other via the microfluidic component. Fluids pass from one macrofluidic chamber through the microfluidic component back to another macrofluidic chamber. The volumes of the chambers are determined by the use of the purified nucleic acids. For example, elution reservoir volume is chosen to allow the final concentration of the purified nucleic acid to be optimal for subsequent reactions.

Following the purification processes in the apparatus of the present invention, the nucleic acid solution provided may be transferred for additional analytic steps. The nucleic acid solution may be automatically transferred to other analytic modules within the same instrument, or the apparatus itself may be transferred to a compatible instrument. Alternatively, the chamber that collects the purified nucleic acid sample may contain a removable nucleic acid storage tube. Samples processed according to this invention may be a precursor to a wide variety of analytical methods, including without limitation nucleic acid fragment sizing, short tandem repeat (STR), Y-STR, and mini-STR, single nucleotide polymorphism, PCR, highly multiplexed PCR, Real-time-PCR, Reverse Transcription PCR, sequencing, hybridization, microarray, VNTR, and RFLP analyses. Similarly, the apparatus, methods, and instruments of the invention can also be applied to immunoassays and protein and mass spectroscopy assays in general and other analytical methods well known to those skilled in the art.

The apparatus of the invention may also have an optional cover to route channels between the drive mechanism of the instrument and each of the individual chambers. In addition, the cover also provides optional functions of venting gases within the chambers to the environment and locking sample collection device following insertion. The cover comprises at least one layer, preferably fabricated of plastic. Additional layers can be added as the number of pneumatic channels or the complexity of routing and other features increases. Layer features can be macrofluidic or microfluidic, and features can be fabricated by CNC machining, hot embossing patterns, die cutting, or laser cutting of plastic sheets, or injection molding of thermoplastic resin. In addition the incorporation of vent membranes into the layer can be achieved by welding and bonding. When two or more layers are required, the individual layers are bonded together to form a single part. Bonding methods for fabrication of the cover include thermal bonding, solvent bonding, ultrasonic bonding, adhesive and laser bonding.

The microfluidic component of the apparatus may contain a variety of fine features or microfluidic elements, including channels (which may be independent, connected, or networked), reservoirs, valves, reaction chambers, liquid and lyophilized reagent storage chambers, mixing chambers, mixing elements, venting elements, access holes, pumps, metering elements, heating elements, magnetic elements, reaction chambers, filtration elements, purification elements, drive lines, actuation lines, optical excitation and detection regions, optical windows. The microfluidic component of the apparatus may use valves for flow control to halt or allow flow of fluids within channels. Valves can be passive or, most preferably, active, and valving approaches for microfluidic devices are well known in the art (reviewed in Zhang, C., et al. (2007) "Micropumps, microvalves, and micromixers within PCR microfluidic chips: Advances and trends." *Biotechnol Adv* 25(5): 483-514). Active valve structures include mechanical (thermopneumatic and shape memory alloy), non-mechanical (hydrogel, sol-gel, paraffin, and ice), and external (modular built-in, pneumatic, and non-pneumatic) microvalves. The pneumatic and mechanical microvalve structures can also apply either elastomeric or non-elastomeric membranes. Passive valves include in-line polymerized gel, passive plug, and hydrophobic valves.

The fluids required for the methods of the invention are nucleic acid purification reagents and gasses (e.g. air, nitrogen, or oxygen). The purification reagents and media can be based on any of the well-characterized methods of the literature, including silica matrices/chaotropic agents (Boom, R. et al., (1990), supra), silica matrices/non-chaotropic agents, ion exchange, and many others as well known in the art. Many such methods are summarized in Current Protocols in Molecular Biology (Edited by Ausubel et al, John Wiley and Sons, 2010). Similarly, many types of purification media can be used in the apparatus. Silica nucleic acid binding membranes, for example, vary in size, pore size, flow rate, retention volume, reagent compatibility, and binding capacity; appropriate membranes are chosen based on a given application. Cell separation media are also selected based on the physical and chemical properties of the cellular material to be separated. Finally, in some cases, particle removal filters may be used, preferably to remove particulates that may inhibit, slow down, or otherwise interfere with a downstream separation or purification process. In many forensic embodiments, particle removal filters are preferred.

The drive mechanism to allow fluid transport throughout the apparatus can be pneumatic, mechanical, magnetic, fluidic, or any other means that allows precise control of the fluid movement. A pneumatic drive allows controlled flow or a controlled pressure or a controlled volumetric displacement of air (or other gasses) to the apparatus via one or more drive lines, and are particularly preferred. The pneumatic drive lines can be utilized to move liquids, create bubbles, burst foils, actuate mechanical features, and perform any other movements required for a given nucleic acid purification method. The drive of the instrument must interface with the drive lines of the apparatus. For a pneumatic drive, the interface may be located at one or more macrofluidic or microfluidic regions of the apparatus. The drive is contained within the instrument, which may also contain a power supply, a housing to accept the apparatus, features that allow ruggedization and protection from environmental exposure, an onboard computer, a process controller, a monitor, and other features based on the nucleic acid analysis to be conducted. The pneumatic drive system may contain the following components: pumps, electromechanical valves, pressure regulators, pressure tanks, tubing, pneumatic manifolds, and flow and pressure sensors. The pneumatic drive system allows the generation and deliver of a defined flow, pressure, or volume to each of the pneumatic lines of the apparatus. A process controller can execute a programmed script following insertion of the unprocessed sample into the apparatus. More than one class of drive mechanism can be utilized with the apparatus. However, the use of a single drive mechanism, preferably pneumatic, reduces the complexity of both the instrument and the apparatus.

Once in the sample chamber, the biological sample may be lysed by a number of methods. Chaotic bubbling is caused by the flow of fluid, preferably air, into a chamber of the macrofluidic component. The flow may be turbulent, which may contribute shearing forces that would contribute to cell lysis and which may be appropriate for mixing or homogenization of reagents. Other approaches to potentiating lysis include mechanical actuation by vibration, ultrasonic actuation, and heat.

In one embodiment of the invention, the nucleic acid to be purified is DNA. Other embodiments are based on the purification of RNA and total nucleic acids. The reagents required to purify DNA, RNA, and total nucleic acids are well-known in the art. See, e.g., Gjerde, D. T. et al., RNA Purification & Analysis: Sample Preparation, Extraction, Chromatography (2009 Wiley-VCH Pub.); Ausubel, F. M. et al., (Eds)., Current Protocols in Molecular Biology (2008 John Wiley Pub.). In another embodiment of the invention, the apparatus contains macrofluidic and microfluidic elements that allow cell separation. These elements may allow a variety of cell separations including white blood cells (WBC) to be separated from red blood cells, bacteria or viruses to be separated from host cells, sperm cells to be separated from vaginal epithelial cells, and intracellular viruses and bacteria to be separated from their mammalian hosts.

The apparatus of the invention can be fabricated in several ways. Based on the time and cost allotted for fabrication and the number of apparatus to be fabricated a variety of methods are available. The apparatus may be fabricated out of glass or more preferably, out of thermoplastic polymers such as polyethylene, polypropylene, polycarbonate, polystyrene, cyclic olefin polymer, and cyclic olefin copolymer. The apparatus may be fabricated in one or more parts, macrofluidic and microfluidic. If the apparatus is made of plastic parts, the components may be bonded together using clamping, thermal bonding, ultrasonic bonding, solvent bonding, laser bonding, or adhesive bonding (bonding methods are reviewed in Tsao and DeVoe, Microfluid Nanofluid (2009) 6:1-16). A rapid and straightforward method of fabrication is by computer-numerical-controlled machining. Other methods include blow molding, extrusion, and embossing.

A preferred method of fabrication is by injection molding. The macrofluidic portion of the apparatus of the invention comprises of a set of chambers of tubular structure that may be injection molded together to form a single part. The top surfaces of each chamber are preferably coupled pneumatically to a cover to provide pneumatic drive to each of the individual chambers. The bottom surfaces of each chamber are preferably coupled pneumatically and fluidically to the microfluidic component. Tube-like structures that have been injection molded as a single part include microtiter plates with 96, 384 and 1536 wells. Microcentrifuge plates with 96 wells in a 12×8 configuration 8.4 mm in diameter and 16 mm deep is described by Turner (U.S. Pat. No. 6,340,589). While these plates have a high density of tubular structures in high packing density, the depth of these tubes are not more 16 mm. PCR tubes-tube strips with 8 or 12 tubes have been fabricated in-line by injection molding, with each tube being 8.65 mm in diameter and 30 mm deep with a capability to hold 0.2 mL. These are all coupled versions of the plastic reaction vessel described by Gerken (U.S. Pat. No. 4,713,219). These strip tubes have a low packing density, and are oriented in-line. Finally, injection molding of two long coupled tubes are described by Spehar (U.S. Pat. No. 4,753,536).

The tubular structures of the macrofluidic portion have thin walls. When injection molded, the macrofluidic portion is essentially a series of thin walled tubes held together as opposed to a solid block with tubes drilled out. The tubes have wall thicknesses of 0.1-5.0 mm, preferably 0.3 to 3.0 mm, more preferably 0.5 to 1.5 mm, still more preferably 0.7 to 1.3 mm, and most preferably 0.9 to 1.2 mm.

The injection molded tubular structures of the macrofluidic portion preferably have a tube length in excess of 16 mm, 18 mm, 20, mm, 25 mm, 30 mm, 40 mm, 50 mm, 60 mm, 70 mm, 80 mm, 90 mm, or 100 mm. The tubular structures are oriented in a two dimensional configuration. The tops of the tubular structures must be flat to achieve strong pneumatic coupling to optional cover, and the bottoms of the tubular structures must be flat to achieve strong pneumatic and fluidic coupling to the microfluidic portion. Spacing of the tubular structures must be maintained to accurately match the footprint of the microfluidic portion. The tubular structures may taper from top to bottom to facilitate precise interfacing with the microfluidic component. Similarly, the form of the tubular structure may be adapted for a particular purpose, such as a narrowed lower portion to facilitate chaotic bubbling and mixing or a narrowed central or upper portion to maintain the position of a sample collection device.

The tubular structures of the macrofluidic component are packed densely, with one tube present per approximately 200 $mm^2$ surface area at the top of the component, more preferably approximately 150 $mm^2$. For other applications, one tube is present, preferably, per approximately 100 $mm^2$ surface area at the top of the component, and most preferably one tube is present per approximately 50 $mm^2$ surface area at the top of the component. Similarly, the surface area occupied by the tubular structures as compared to the total area at the top of the macrofluidic component is greater than 30%, more preferably greater than 40%. For other applications, greater than 50%, for other applications still more preferably greater than 60%, and most preferably greater than 90%.

The total volume of the apparatus is based in part on the number and volume of chambers and the number of samples to be processed simultaneously. The volume will be at least 2 mL, and may be 45 mL, 65 mL, 100 mL, 500 mL, 1000 mL, 1500 mL or more, and preferably in the range of 45-1500 mL, and even more preferred in the range of 65-1500 mL.

The apparatus of the invention can accept and process one or more samples. For some embodiments the apparatus may be configured to accept 2, 4, 8, 16, 24, 36, 48, 96, 192, or 384 samples. As the number of units increases, the approach to manufacturing may change. For example, a single sample unit fabricated by injection molding may be used as the basis for a 5-sample apparatus. Sets of 5-sample apparatus can be bonded, generating 10-sample, 15-sample apparatus. Alternatively, a 15-sample apparatus can be manufactured as a single large unit. The apparatus, instruments, and methods of the invention allow the rapid purification of nucleic acids. From the time the process is initiated following insertion of the unprocessed sample to the time purified nucleic acids from the sample are generated is preferably less than 30 minutes, more preferably less than 20 minutes, even more preferably less than 10 minutes, and most preferably less than 5 minutes.

EXAMPLES

Example I

Extracellular Bacteria Present in Blood

Pathogens such as staphylococci, streptococci, and *Yersinia enterocolitica* may be present in the blood. In some cases, it is advantageous to isolate extracellular pathogens from the cellular elements of human (or other animal host) blood. For example, in order to make best use of the advantages of a microfluidic device, an ideal volume for the purified DNA that is the end product of the DNA extraction/purification module is 25 µL or less. This volume can be quickly transferred and manipulated on a microfluidic chip. By limiting this volume, however, an analogous limit is also placed on the maximum amount of DNA that can be present within that volume. In 3 mL of whole blood, assume a total of 15 million white blood cells and 150 bacteria (50 per mL). The total DNA in this sample is approximately 90 µg, with essentially all of this due to leukocyte DNA. If this DNA were purified and recovered with 100% efficiency in a solution of 25 µL, the DNA concentration would be 3.6 mg/mL, almost certainly inhibitory for PCR (F. B. Cogswell, C. E. Bantar, T. G. Hughes, Y. Gu, and M. T. Philipp (1996) "Host DNA can interfere with detection of *Borrelia burgdorferi* in skin biopsy specimens by PCR" *J Clin Microbiology* 34:980-982) and too viscous for microfluidic manipulation. In contrast, the small amount of bacterial DNA—only 250 genomes of approximately 5 Mbp/genome—present in 25 µL would be approximately 1 pg. If only one-tenth of the total DNA were to be used for the microfluidic reaction, the limit of detection would by definition decrease ten-fold. As blood volume increases, the number of leukocytes per unit blood volume increases, the microfluidic solution volume decreases, and the number of organisms per sample decrease, this problem becomes even more severe. The conclusion from this analysis is that in certain applications (particularly those in which bacterial load is low early in an infection), most of the leukocyte DNA should be removed before the final microfluidic volume is reached. This would allow most or all of the pathogen DNA to be analyzed following purification. Similarly, background environmental DNA such as that which accumulates on the filters of air breathers can interfere with the sensitivity and specificity of pathogen identification.

Removal of leukocytes in 3 mL of fresh human whole blood was achieved by stacking 13 layers of binding media with nominal pore size of 8 µm (Leukosorb B media, Pall Corporation, Port Washington, N.Y.) and filtered using initial vacuum pressure of 0.25 psi and then was increased to 25 psi for final collection of filtrate. Useful pore sizes of binding media can range from less than 1 micron to over 100 microns, depending on the type of cells, virions, bacteria, fungi, and particulates to be separated. Recovered volume was approximately 1.5 mL with filtration completed in 1 minute. WBC counting of filtrates indicated that greater than 99% of leukocytes were retained by the filter.

3 mL of fresh human whole blood samples were spiked with 100 µL of *B. subtilis* (ATCC® 7003™), with each 100 µL containing varying concentrations of *B. subtilis* per sample. In this experiment, *B. subtilis* was used as a model for pathogenic organisms and biothreat agents (e.g. *B. anthracis*). These blood-bacteria samples were passed through the stacked media using the apparatus of FIG. 1. Sample application was followed by wash with 3 mL TSB (Tryptic Soy Broth media), allowing retrieval of bacteria that did not initially pass through the binding matrix. Collected flow-through of approximately 4.5 mL was passed through a single layer of 0.2 µm polycarbonate track-etch membrane (SPI-Pore™ Track-Etch Membrane, Structure Probe, Inc., West Chester, Pa.) to concentrate the bacteria through capture on the membrane. This concentration method reduced reagent volumes, sizes of the purification cartridge reservoir chambers, and process time. The captured organisms were collected from the surface of the membrane by resuspending in 100 µL PBS (Phosphate-buffered saline).

Figure 2:
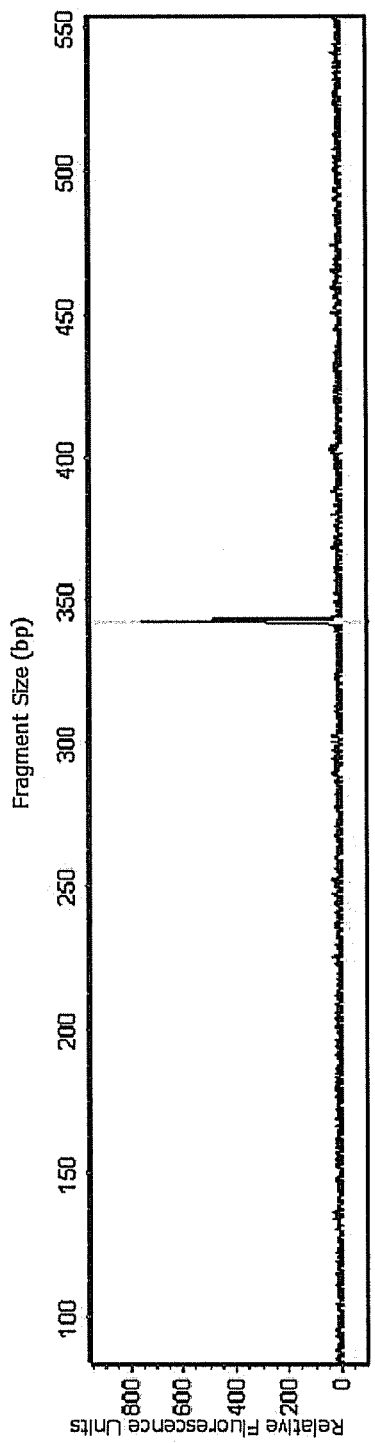
FIG. 2 is an electropherogram showing near-quantitative recovery of *B. subtilis* using a purification cartridge.

In this embodiment, the lysis of bacterial cells was based on chaotropic salt extraction method for DNA and RNA. In particular, the preferred lysis buffer solution contained 4 M guanidinium hydrochloride, 80 mM Tris-HCl (pH 7.5), 20 mM EDTA and 5% Triton X-100 (other useful lysis buffers are described in Ausubel et al., supra). To 100 µL of resuspended organisms, 450 µL of lysis buffer with 1 mg/mL final concentration of proteinase K was transferred and mixed thoroughly in the purification cartridge through the chaotic bubbling method defined in the pneumatic script. To this, 550 µL of absolute (200 proof) ethanol was added and again mixed by bubbling. The lysate was passed microfluidically through a silica-based membrane for DNA binding in the microfluidic portion of the purification apparatus. After the entire lysate was filtered, the membrane is washed with 2 mL of 1× wash solution prepared by mixing 1 unit volume of 200 mM NaCl solution, 0.5 unit volume of 200 proof ethanol and 0.5 unit volume of >99% isopropanol. Following wash step, the membrane was then allowed to dry for 1 minute by exposure to air from the pneumatic system. DNA was finally eluted in 20 µL TE buffer, pH 8.0. Pressures for lysate filtration, membrane washing and drying, and elution were approximately 5 psi. Fast PCR amplification (Giese, H. et al., (2009), "Fast multiplexed polymerase chain reaction for conventional and microfluidic short tandem repeat analysis" J Forensic Sci 54(6): 1287-97) using glnA (glutamine synthetase) primers in a microfluidic biochip and separated and detected microfluidically results in the expected 343-bp fragment characteristic of the *B. subtilis* glnA gene with signal intensity proportional to the input copies in blood samples. PCR was performed using biochips and a fast thermal cycler as described in "Methods for Rapid Multiplexed Amplification of Target Nucleotides," PCT/US08/04487, which is hereby incorporated by reference. Separation and detection were performed on Genebench as described in "Plastic Microfluidic Separation and Detection Platforms," PCT/US08/04405, and "Integrated Nucleic Acid Analysis," PCT/US08/04462, both of which are hereby incorporated by reference. FIG. 2 shows an electropherogram showing approximately 2 genome equivalents of *B. subtilis*; this represents the amplification of only ~6% of the total material recovered from a 33 cfu/mL blood sample and using 40% of the PCR product for electrophoretic analysis. Bacterial recovery is near-quantitative.

An alternative method for quantitation was to use a Petroff-Hausser chamber. Collected flow-through was plated on TSB-agar plates to determine the effect of filtration through stacked media on the recovery of bacteria. Recovered bacteria are normalized using plating efficiency based on colonies recovered in unfiltered control samples. At clinical relevant concentrations of bacteria in blood, approximately 100% of the bacteria were recovered.

| Expected Bacteria in 3 mL of Blood | # of Colonies Recovered by Plating Filtered Samples | % Recovery | % Recovery Normalized |
| --- | --- | --- | --- |
| ~1000 | 860 ± 239 | 85 ± 18 | 104 ± 10 |
| ~100 | 88 ± 16 | 88 ± 11 | 97 ± 17 |
| ~10 | 9 ± 2 | 96 ± 19 | 103 ± 26 |

Figure 3:
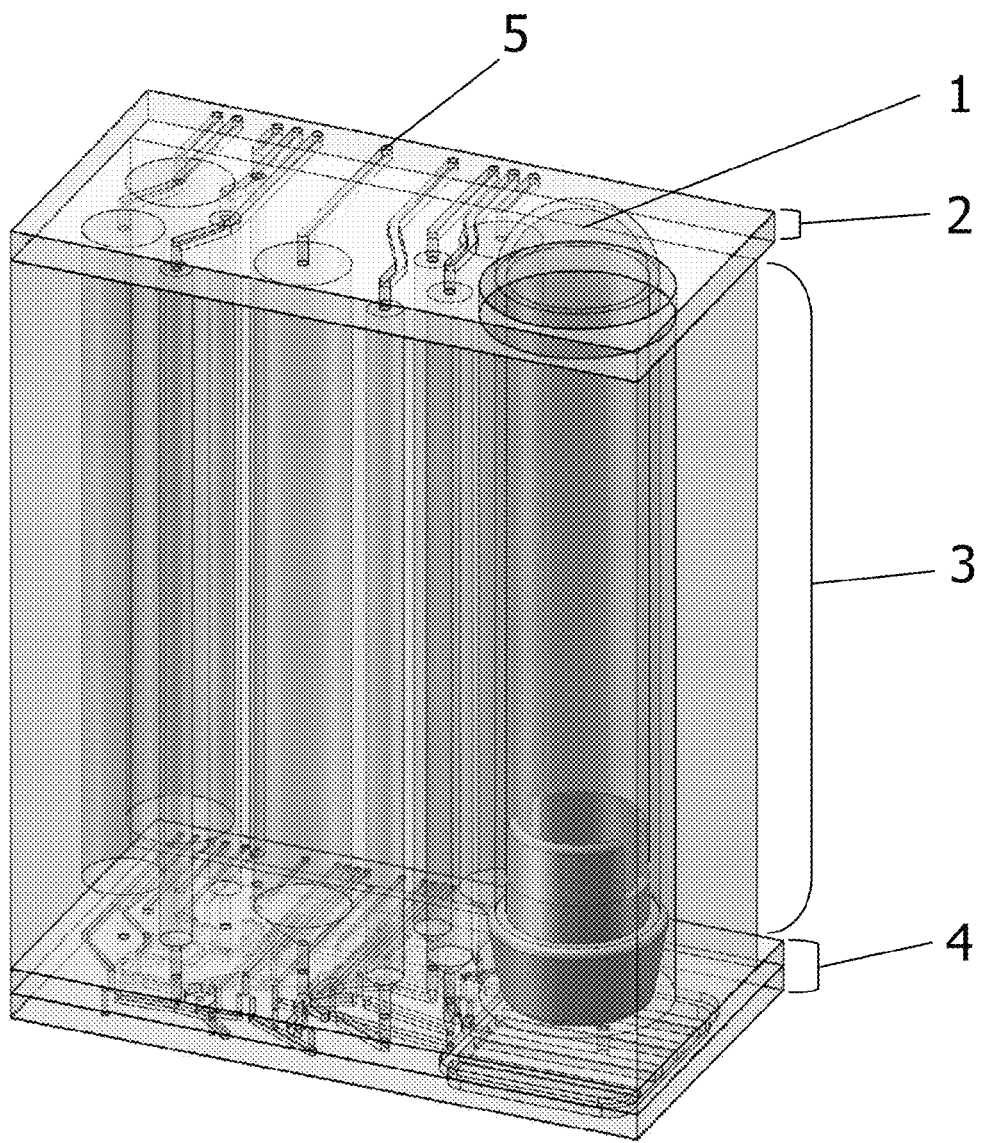
FIG. 3 is a side view of a purification cartridge for blood samples. The blood collection tube is labeled 1, the cover is labeled 2; the macrofluidic component is labeled 3; the microfluidic component is labeled 4; a pneumatic interface port is labeled 5.
Figure 4:
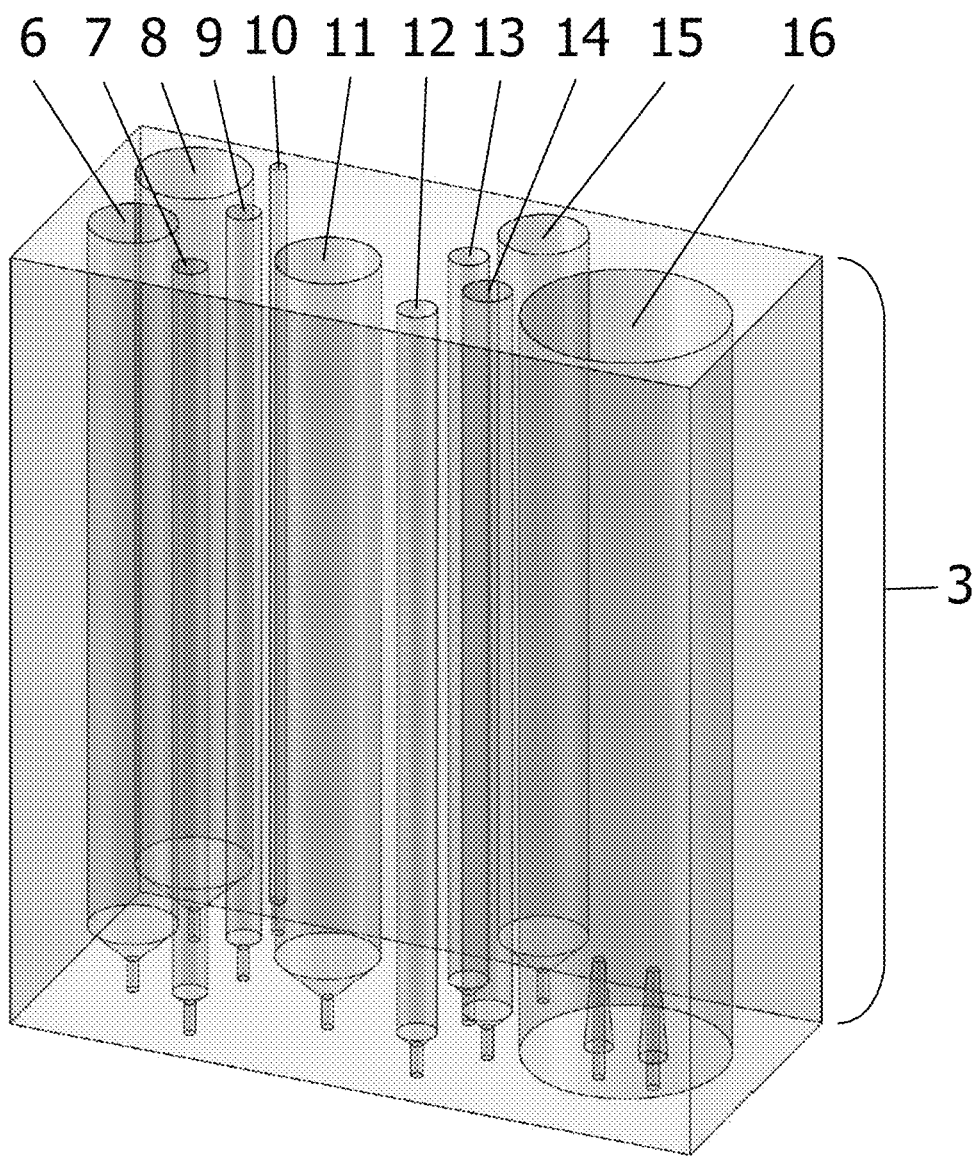
FIG. 4 is a side view of the macrofluidic component of a purification cartridge for blood samples. The macrofluidic component is labeled 3; the first wash reservoir is labeled 6; the eluate homogenization chamber is labeled 7; the waste chamber is labeled 8; the eluate reservoir is labeled 9; the resuspension solution reservoir is labeled 10; the lysis chamber is labeled 11; the ethanol reservoir is labeled 12; the lysis reservoir is labeled 13; the holding chamber is labeled 14; the second wash reservoir is labeled 15 and the blood collection tube cavity is labeled 16.
Figure 5:
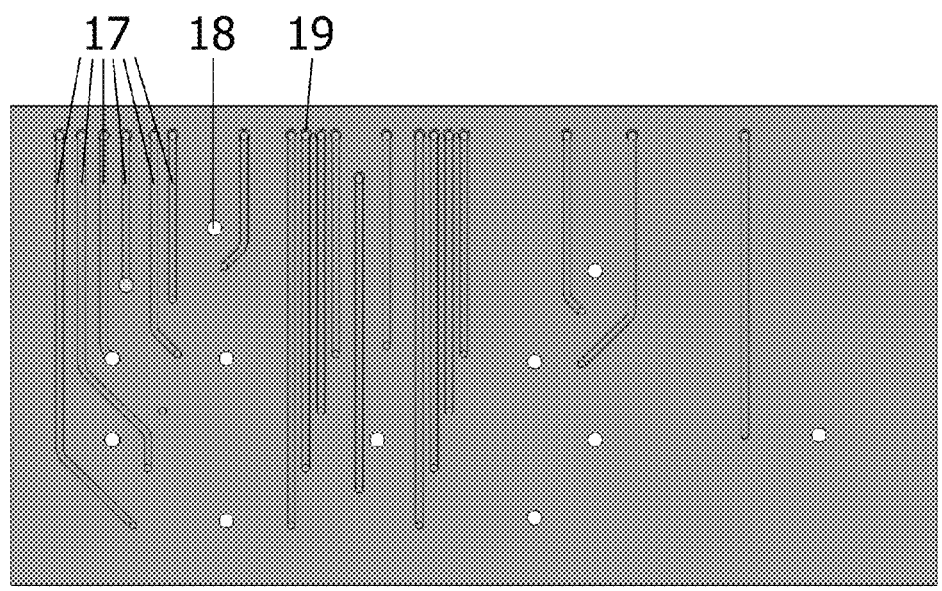
FIG. 5 is a top view of the pneumatic layer of a purification cartridge for blood samples. Pneumatic channels are labeled 17; through holes to reagent reservoirs and chambers of the macrofluidic component are labeled 18 and pneumatic interface ports are labeled 19.
Figure 6:
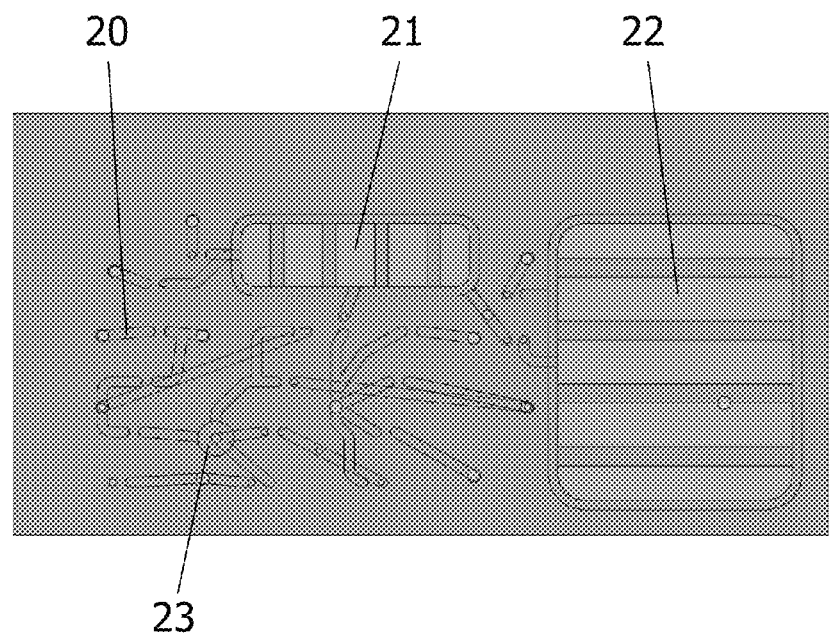
FIG. 6 is a top view of the microfluidic layer of a purification cartridge for blood samples. Fluidic channels are labeled 20; the track etch membrane is labeled 21; the Leukosorb filter is labeled 22 and the purification filter is labeled 23.

FIG. 3 shows an integrated purification cartridge for blood samples. FIGS. 4, 5, and 6 show the macrofluidic component, pneumatic layer of the microfluidic component, microfluidic layer of the microfluidic component, respectively, of the integrated purification cartridge. The macrofluidic portion [3] of the apparatus is composed of 11 chambers, [6] to [16], that hold preloaded reagent solutions or serve as holding/reaction chambers during the DNA purification process. One chamber is used to accept the blood collection tube; six chambers are pre-filled with 3 mL of wash buffer, 100 µL of resuspension solution, 450 µL of lysis solution, 550 µL of absolute ethanol, 2 mL of wash buffer and 20 µL of TE (pH 8) elution buffer.

The apparatus accepts a standard 3 cc vacutainer tube (for separation experiments, blood should be collected in tubes containing appropriate anticoagulants. The blood collection tube [1] is inserted into the cartridge with the rubber stoppered end down. The purification process is initiated when the user presses a start button. The apparatus together with the instrument execute an automated script and generate purified DNA. Within the instrument, the blood collection tube is pushed onto two hollow pins located at the base of blood collection tube cavity [16]. The hollow pins pierce through the rubber stopper to fluidically and pneumatically couple the blood collection tube to the apparatus. The blood collection tube [16] is pressurized pneumatically to 5 psi to drive the blood from the blood collection tube [16] through the leukosorb filter [22] and track-etch membrane [21] to the waste chamber [8]. The filtrate that passes through the leukosorb filter contains the biological material (e.g. bacterial, viral, or fungal pathogens) for analysis, a leukocyte-reduced filtrate. This filtrate is then driven through a track-etch membrane, and the pathogens of interest are retained by the membrane (the pore size of the pathogen capture membrane is elected based on the dimensions of the pathogens to be analyzed). Wash solution from wash reservoir 2 [15] is pneumatically driven through the leukosorb filter [22] and track-etch membrane [21] to the waste chamber [8]. Resuspension solution from the resuspension solution reservoir [4-10] is applied to the surface of the track-etch membrane [6-21]. This solution will resuspend the pathogens retained on the track etch membrane, generating a concentrated pathogen suspension (which may also include residual leukocytes). This suspension is pneumatically driven into the lysis/waste chamber [11]. Lysis reagent is pneumatically driven into the lysis chamber [11]. Air is pneumatically driven into the lysis/waste chamber [11] to effect chaotic bubbling of the lysate within the lysis/waste chamber [11]. This bubbling creates flow of the lysate to mediate cell lysis. Ethanol from the ethanol reservoir [12] is driven into the lysis/waste chamber [11]. Continued application of pneumatic drive through the ethanol reservoir [12] after all the ethanol has been dispensed forces air through the lysate and ethanol solution to effect mixing by chaotic bubbling. All the lysate and ethanol mixture is pneumatically driven into the holding chamber [11]. From the holding chamber [11] the lysate and ethanol mixture is pneumatically driven through the purification membrane [23] and into the lysis/waste chamber [11]. Wash solution from wash reservoir 1 [6] is pneumatically driven through the purification membrane [23] and into the lysis/waste chamber [11]. This wash removes unbound material and residual lysis solution. Continued application of pneumatic drive through the wash chamber [6] after all the wash solution has been dispensed will force air through the purification filter and dry the filter. Elution solution is pneumatically driven from the eluate reservoir [9] through the purification membrane [6-23] to the eluate homogenization chamber [7]. Continued application of pneumatic drive through the eluate reservoir [9] after all elution solution has been dispensed will force air through eluate homogenization chamber [7] to effect mixing by chaotic bubbling. Homogenized purified DNA solution in the eluate homogenization chamber [7] is ready for subsequent analysis.

Example II

Intracellular Bacteria Present in Blood

Certain bacteria such as *Francisella tularenis* and *Chlamydia trachomastis* spend a significant portion of their life cycles within mammalian cells. Some are obligate intracellular organisms and others are optionally intracellular. A comprehensive summary of known human pathogens is provided by Gorbach, S. L. (et al. Eds.) Infectious Disease (3rd Ed), (2004 Lippincott Williams & Wilkins Pub). The DNA purification process for such intracellular bacteria in blood is similar to that of extracellular bacteria with a major exception. Following application of whole blood on and through the cell separation filter, the leukocytes trapped by the filter contain the DNA of interest. The filter is washed, resuspended in 100 µL, and subjected to guanidinium-based purification as described in Example I with corresponding reduction is reagent volume.

If desired, the apparatus can be design to initially lyse the leukocytes (osmotically, for example), taking advantage of the relative ease of lysis of mammalian cells as compared to bacteria. In this setting, the intact intracellular bacteria are released, and the cell extract is based through a bacterial capture filter and washed. Bacterial DNA is then purified as described in Example I. Similarly, whole blood can be lysed in the absence of cell separation, allowing extracellular or intracellular bacterial or viral DNA to be purified.

Example III

Purification of DNA from Biological Sample(s) Collected by a Validated Forensic Collection Swab Forensic samples can be broadly divided into two types; casework samples are those that are collected at a crime scene or in connection with an investigation, and reference samples are collected directly from an individual. Several collection methods are available based on the specific type of sample to be analyzed and are designed to obtain and protect biological evidence from the crime scene. Swabbing is a well-established forensic sample collection method, and commercially available swabs have collection matrices consisting of various materials such as cotton, modified cellulose, foam, nylon, polyester and rayon.

Figure 7:
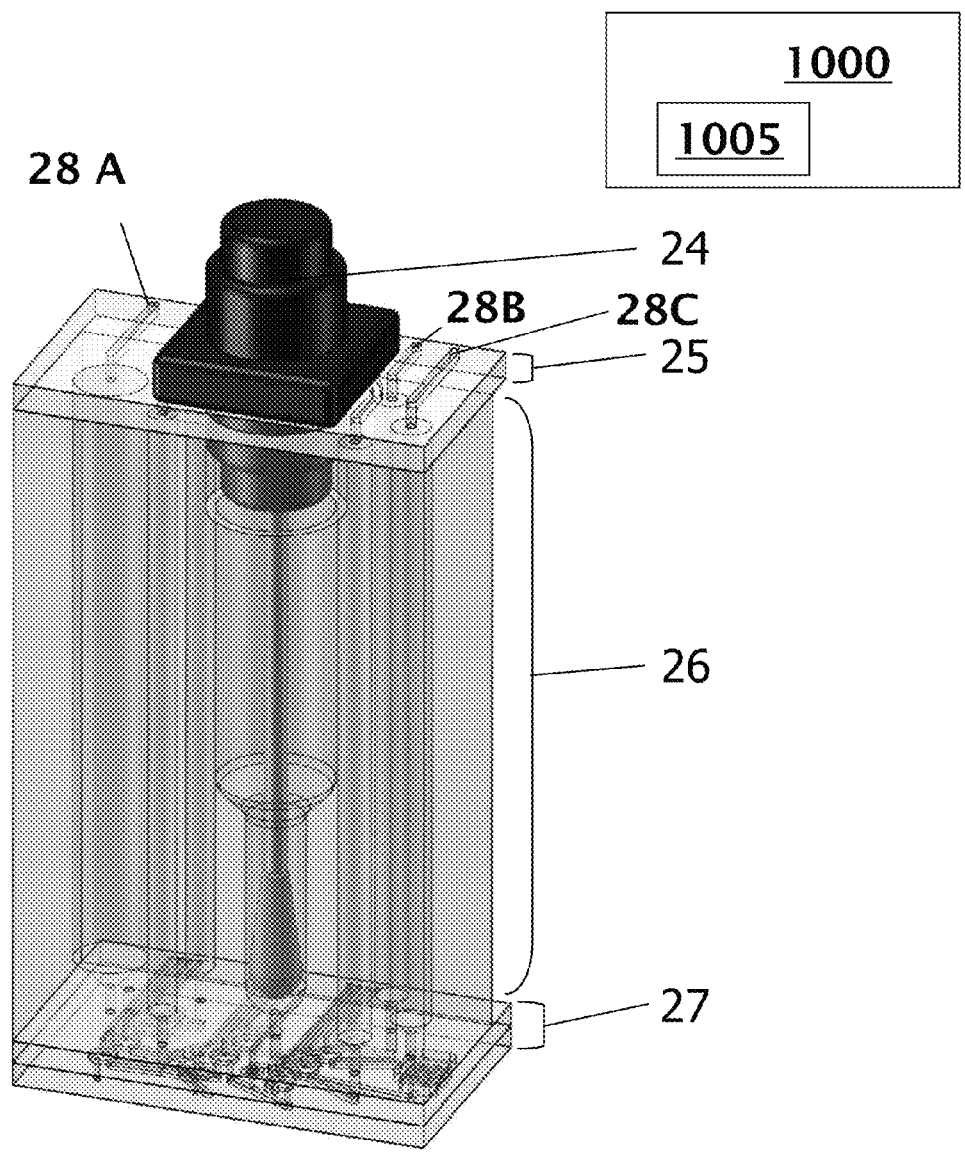
FIG. 7 is a side view of a forensics cartridge. The swab cap is labeled 24; the cover is labeled 25; the macrofluidic component is labeled 26; the microfluidic component is labeled 27; the pneumatic interface ports are labeled 28A, 28B, and 28C; the instrument is labeled 1000 and the drive mechanism is labeled 1005.
Figure 8:
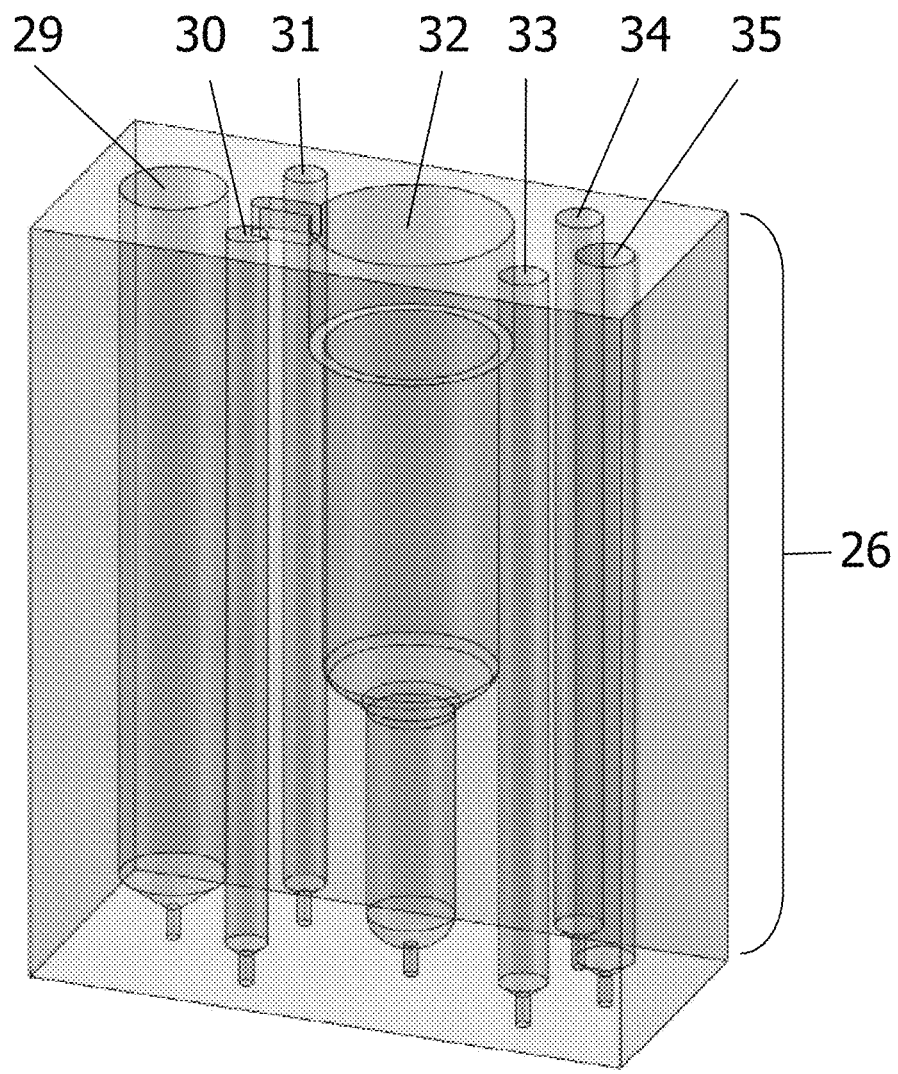
FIG. 8 is a side view of the macrofluidic component of a forensics cartridge. The macrofluidic component is labeled 26; the wash reservoir is labeled 29; the eluate homogenization chamber is labeled 30; the eluate reservoir is labeled 31; the swab chamber is labeled 32; the ethanol reservoir is labeled 33; the lysis reservoir is labeled 34 and the holding chamber is labeled 35.
Figure 9:
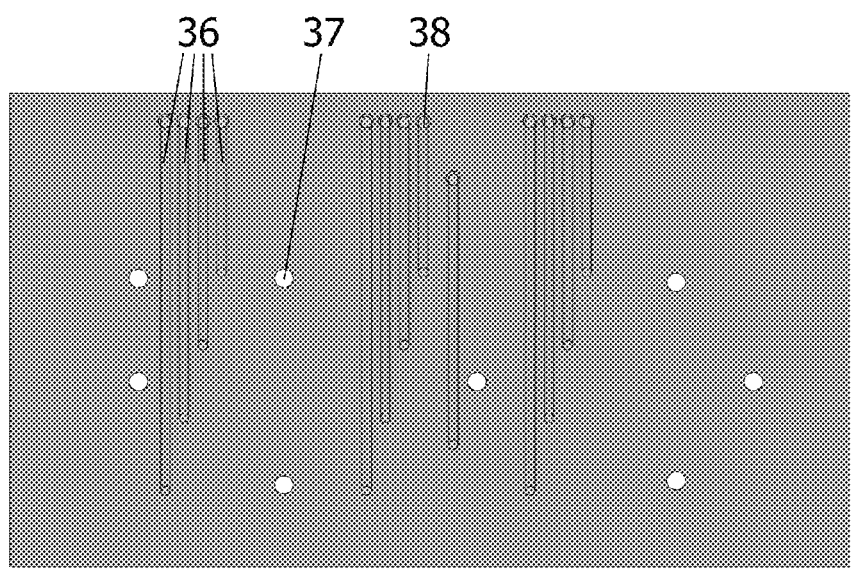
FIG. 9 is a top view of the pneumatic layer of a forensics cartridge. Pneumatic channels are labeled 36; through holes to reagent reservoirs are labeled 37 and pneumatic interface ports are labeled 38.
Figure 10:
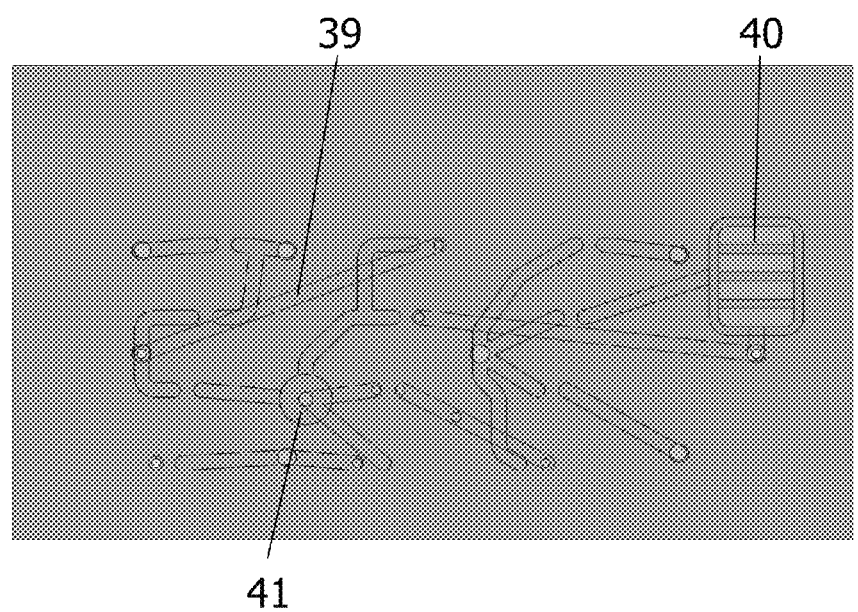
FIG. 10 is a top view of the microfluidic component of a forensics cartridge. Fluidic channels are labeled 39; the particulate filter is labeled 40 and the purification filter is labeled 41.

FIG. 7 shows a purification cartridge for forensic swab samples. FIGS. 8-10 show the macrofluidic component, pneumatic layer of the microfluidic component, and the microfluidic layer of the microfluidic component of the purification cartridge. The microfluidic portion [27] of the purification cartridge contains valves to control the flow of the solutions to and from the macrofluidic portion [26], a particulate filter [40], and a purification filter [41].

To purify DNA from a forensic swab sample, a BodeSecur swab was manually inserted into the sample collection chamber of the purification cartridge and was locked into place for sample processing. The chamber that accepts the swab was designed to allow the swab cap to fit snugly. The cartridge was designed to allow the operator to insert the swab into the chamber and initiate DNA purification without further user manipulation.

The macrofluidic portion of the purification cartridge was composed of 7 chambers that hold preloaded reagent solutions or serve as holding/reaction chambers during the DNA purification process. One chamber was used to hold the cotton swab with the DNA sample; four chambers were pre-filled with 550 µL of lysis solution, 550 µL of absolute ethanol, 2 mL of wash buffer and 100 µL of TE (pH 8) elution buffer. The microfluidic portion of the purification cartridge contained valves to control the flow of the solutions to and from the macrofluidic portion, a particulate filter, and a purification filter.

The sample collection swab (Bode SecurSwab) [24] is comprised of a cap, cotton swab head, and a shaft connecting the two; the total length of this sample collection device is approximately 9.1 cm. The swab head has a nominal dimension of 5 mm to 5.1 mm in diameter and is approximately 12 mm long. When the SecurSwab is inserted into the apparatus, the swab head enters a tubular section of the sample chamber and is positioned between 0 mm to 1.5 mm from the bottom of the sample chamber. The tubular section is 5.85 mm in diameter and 24 mm in length. An air inlet port that is 1 mm in diameter is located at the bottom of the tubular section. The diameter of the inlet port (between 0.1 mm and 2.5 mm and preferably between 0.7 mm and 1.3 mm) and the dimensions of the tubular section of the sample chamber can be modified to optimize fluid flow and chaotic bubbling.

The purification process was initiated by simply pressing a button that starts the automated script that controls the pneumatic drive [1005] on the instrument [1000]. The pneumatic drive [1005] applies the required pressures and vacuums for the required times to enable all process steps to be conducted automatically, without user intervention. Lysis solution was pneumatically driven through interface port [28B] from the lysis reagent reservoir [34] into the swab chamber [32] and brought in contact with the swab. Continued application of pneumatic drive through interface port [28B] through the lysis reservoir [34] after all the lysis reagent had been dispensed forced air through swab chamber effect "chaotic bubbling". This was carried out, by the application of 5.7 psi pressure for 60 seconds. This bubbling created turbulent flow around the swab head, mediating cell lysis and the removal of cellular material from the swab head. Ethanol from the ethanol reservoir [33] was driven into the swab chamber [32]. Continued application of pneumatic drive through the ethanol reservoir [32] after all the ethanol had been dispensed forced air through the lysate and ethanol solution to effect mixing by chaotic bubbling for 30 seconds. All of the lysate and ethanol mixture was pneumatically driven in through interface port [28C] through a particulate filter [40] into the holding chamber [35]. From the holding chamber [35] the lysate and ethanol mixture was pneumatically driven in through interface port [28A] through the purification membrane [41] and into the swab chamber [32]. The swab chamber now served as a waste chamber for spent process reagents. Wash solution from wash reservoir [29] was pneumatically driven through the purification membrane [41] and into the swab chamber [32]. Washing of the purification membrane with wash buffer was conducted to remove unbound material (including protein) and residual lysis solution. Continued application of pneumatic drive via interface port [28A] through the wash reservoir [29] after all the wash solution had been dispensed forced air through the purification filter [41] (i.e., purification filter comprising nucleic acid purification matrix) and dried the filter for 105 seconds. Elution solution was pneumatically driven from the eluate reservoir [31] through the purification membrane [41] to the eluate homogenization chamber [30]. Continued application of pneumatic drive through the eluate reservoir [31] after all elution solution had been dispensed forced air through eluate homogenization chamber [30] to effect mixing by chaotic bubbling. Homogenized purified DNA solution in the eluate homogenization chamber [30] was ready for subsequent analysis.

To evaluate the DNA generated by the purification cartridge, rapid multiplex PCR reactions were performed as described in Geise et al. 2009 (supra) using AmpFlSTR® Identifiler® primers (Life Technologies) in a volume of 7 μL in approximately 17 minutes. Amplified products were separated and detected using NetBio's Genebench. To 2.7 μL of each amplified product 10.2 μL Hi-Di formamide and 0.1 μL of Genescan 500 LIZ internal lane standard (both Life Technologies) were added. After denaturation at 95° C. for 3 min and snap cooling on ice, samples were loaded into the wells of the separation biochip and electrophoretically moved into the separation channels by applying a 350 V/cm electric field for 90 seconds. This was followed by the application of a 150 V/cm electric field along the separation channel to separate the DNA fragments. All separations were carried out at 50° C. Raw data were analyzed with the GeneMarker® HID STR Human Identification Software, Version 1.51 (SoftGenetics LLC, State College, Pa.).

Figure 11:
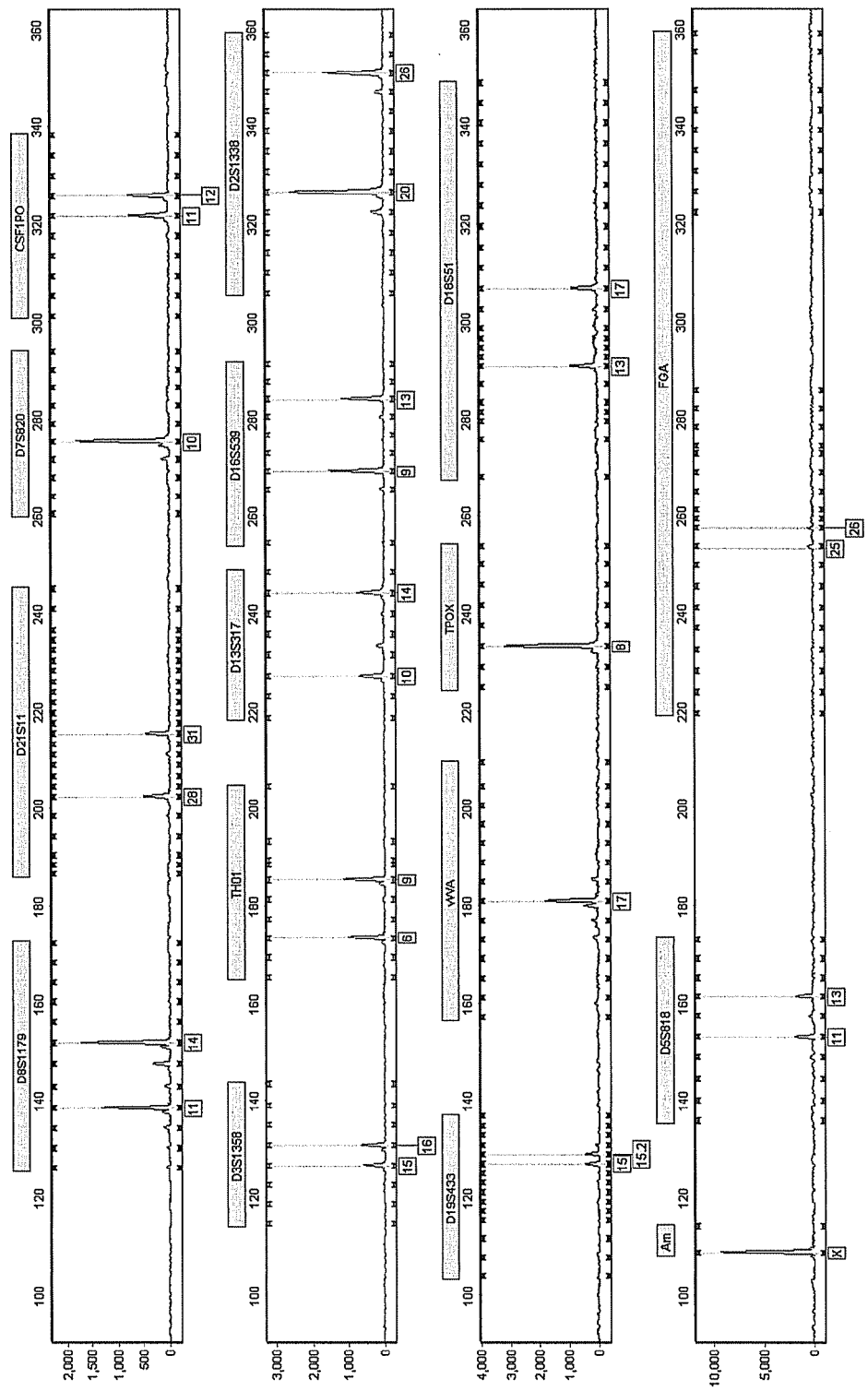
FIG. 11 is an STR profile obtained from DNA purified from a buccal swab.
Figure 12:
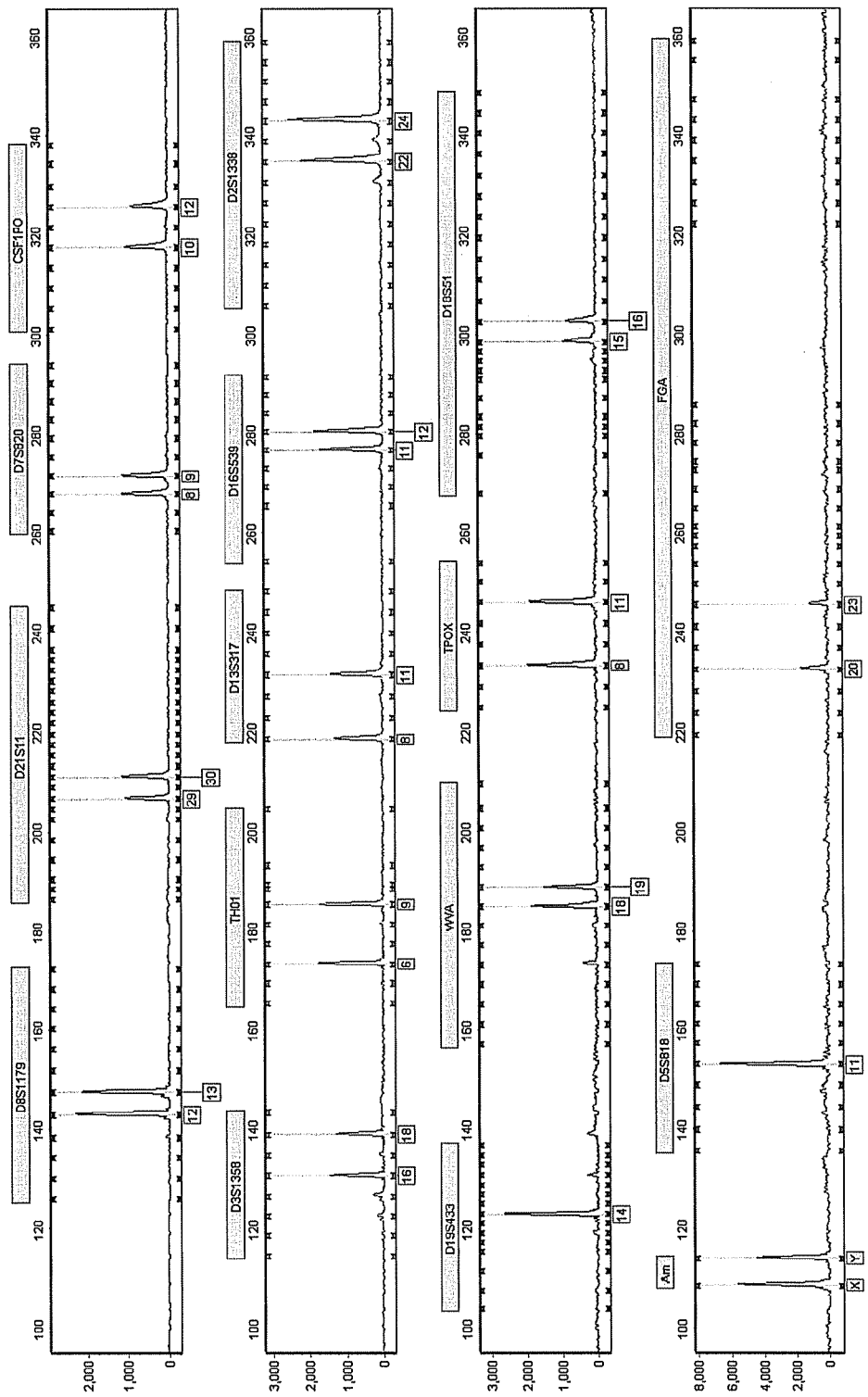
FIG. 12 is a STR profile obtained from DNA purified from a dried bloodstain sample.
Figure 13:
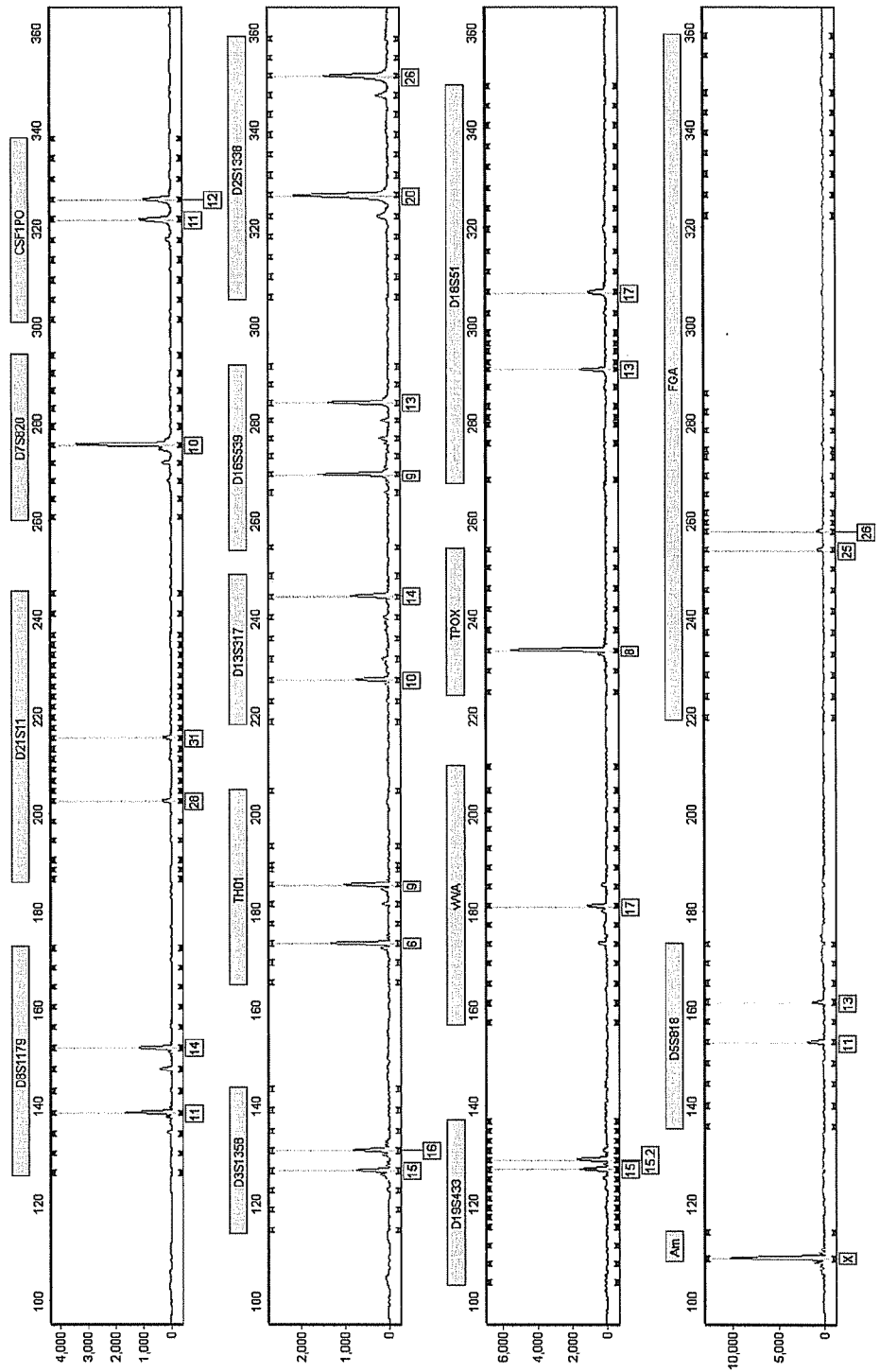
FIG. 13 is an STR profile obtained from DNA purified from saliva isolated from saliva.
Figure 14:
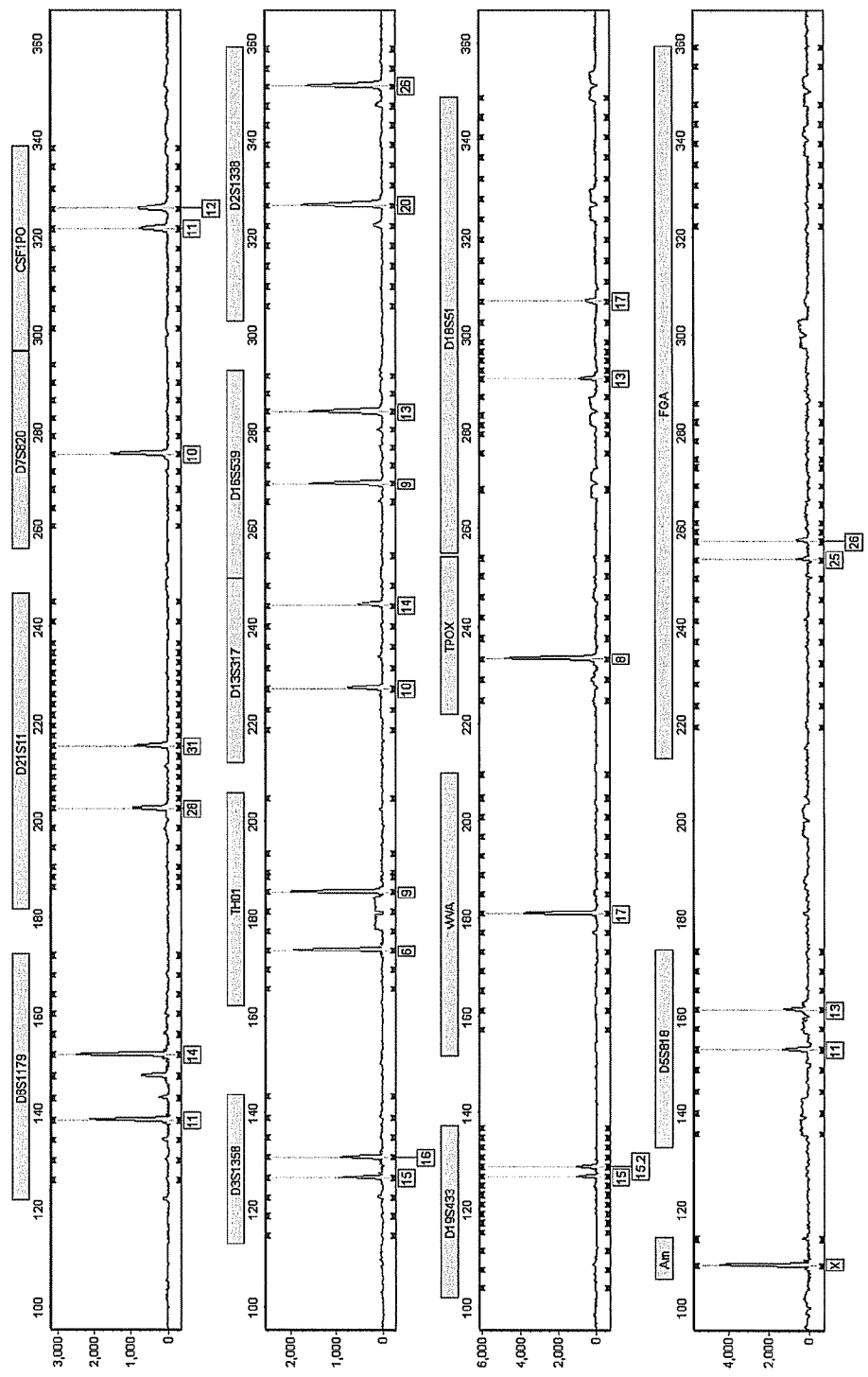
FIG. 14 is an STR profile obtained from DNA purified from a touch sample.

Full allelic profiles from various swab samples (buccal swabs, dried and wet whole blood in swabs, saliva and cellular touch) were generated. Buccal cell samples (FIG. 11) are obtained by lightly scraping the swabs on the inside cheek of a human subject. Dried blood sample are prepared by swabbing dried bloodstains (FIG. 12). Saliva samples (FIG. 13) are collected by swabbing saliva present on a ceramic tile. Touch samples (FIG. 14) are prepared by swabbing a ceramic tile that was handled by a single donor. The swab head was pre-wet with sterile DI water.

Example IV

Bacterial DNA from a Vaginal Swab

A vaginal swab is inserted into the purification cartridge sample chamber through a clamping port to hold the swab in place. The purification is essentially the same as that described for forensic swabs in Example III; the main difference is that the sample chamber is modified to accept and secure the vaginal swab. The geometry of the swab chamber can be modified to accommodate essentially any swab type, regardless of the dimensions of the swab handle or collection region of the swab. The sample chamber is designed such that the swab can be directly inserted into the purification cartridge for processing. The cap of the swab may be modified to lock irreversibly to minimize the possibility of sample-to-sample contamination, and the swab assembly may be modified to allow sample identification (e.g. by bar-code or RFID chip).

Figure 15:
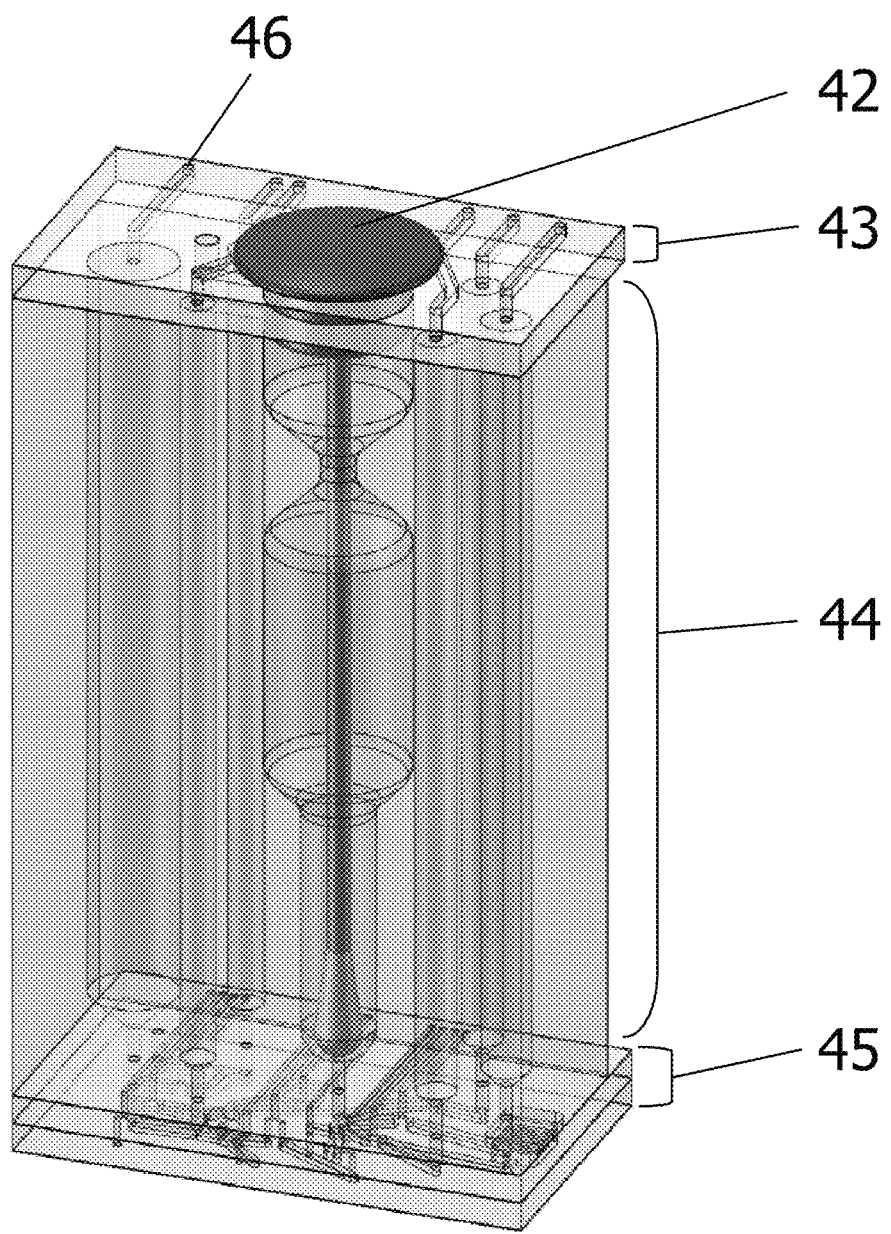
FIG. 15 is a side view of a cervical swab cartridge. The swab cap is labeled 42; the cover is labeled 43; the macrofluidic component is labeled 44; the microfluidic component is labeled 45 and a pneumatic interface port are labeled 46.
Figure 16:
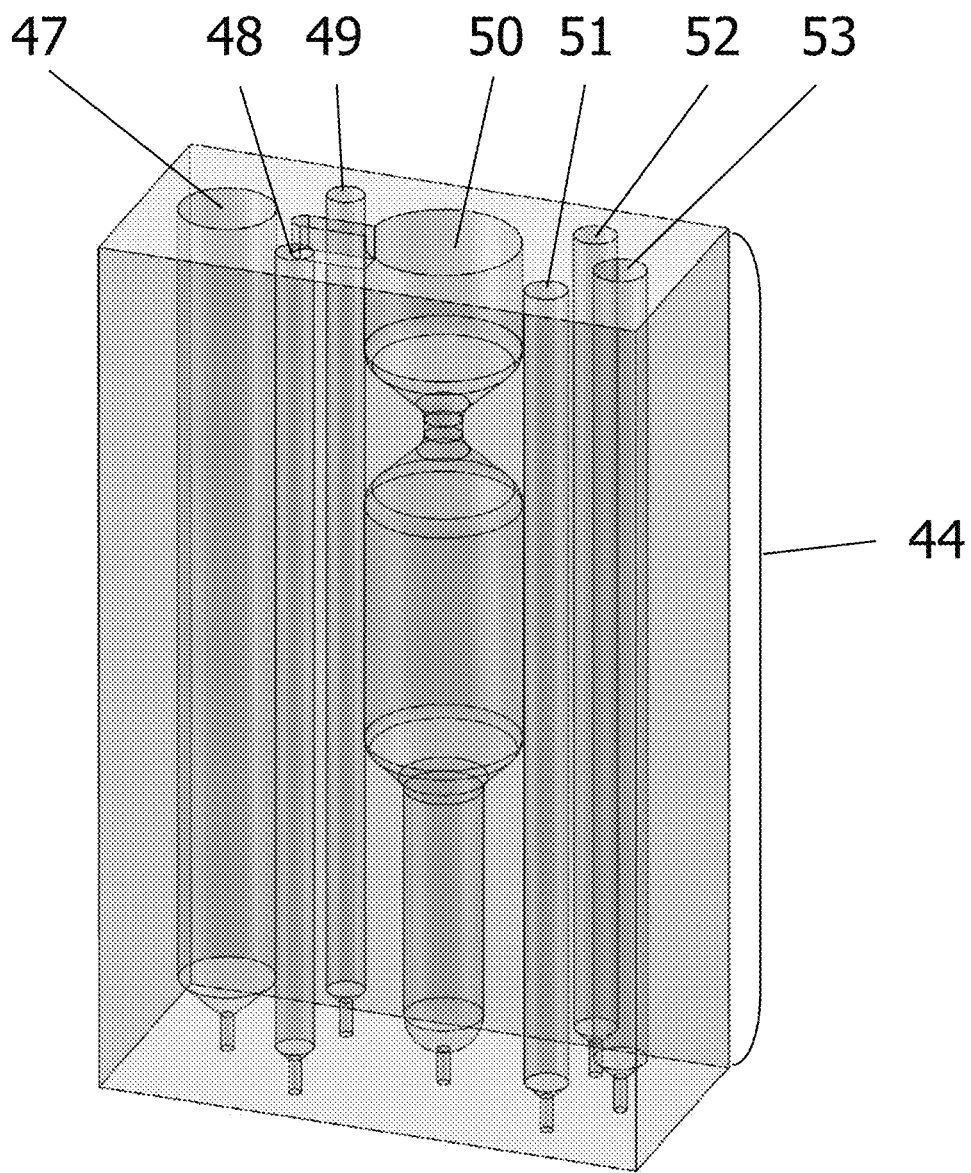
FIG. 16 is a side view of the macrofluidic portion of a cervical swab cartridge. The wash reservoir is labeled 47; the eluate homogenization chamber is labeled 48; the eluate reservoir is labeled 49; the swab chamber is labeled 50; the ethanol reservoir is labeled 51; the lysis reservoir is labeled 52; the holding chamber is labeled 53.

FIG. 15 shows a purification cartridge for vaginal or cervical swab samples and FIG. 16 shows the macrofluidic portion of that cartridge. The microfluidic layers are essentially the same as those of FIGS. 9 and 10.

The macrofluidic portion of the purification cartridge is composed of 7 chambers that hold preloaded reagent solutions or serve as holding/reaction chambers during the DNA purification process. One chamber is used to hold the cotton swab with the DNA sample; four chambers are pre-filled with 550 μL of lysis solution, 550 μL of absolute ethanol, 2 mL of wash buffer and 100 μL of TE (pH 8) elution buffer.

The purification process is initiated by simply pressing a button that starts the automated script that controls the pneumatic drive. The pneumatic drive applies the required pressures and vacuums for the required times to enable all process steps to be conducted automatically, without user intervention. Lysis solution is pneumatically driven from the lysis reagent reservoir [52] into the swab chamber [50] and brought in contact with the swab. Continued application of pneumatic drive through the lysis reservoir [52] after all lysis reagent has been dispensed will force air through swab chamber effect "chaotic bubbling" at 5 psi for 60 seconds. This bubbling creates turbulent flow around the swab head, mediating cell lysis and the removal of cellular material from the swab head. Ethanol from the ethanol reservoir [51] is driven into the swab chamber [50]. Continued application of pneumatic drive through the ethanol reservoir [51] after all the ethanol has been dispensed will force air through the lysate and ethanol solution to effect mixing by chaotic bubbling for 30 seconds. All the lysate and ethanol mixture is pneumatically driven through a particulate filter [40] into the holding chamber [35]. From the holding chamber [35] the lysate and ethanol mixture is pneumatically driven through the purification membrane and into the swab chamber [50]. The swab chamber now serves as a waste chamber for spent process reagents. Wash solution from wash reservoir [47] is pneumatically driven through the purification membrane and into the swab chamber [50]. Washing of the purification membrane with wash buffer is conducted to remove unbound material (including protein) and residual lysis solution. Continued application of pneumatic drive through the wash reservoir [47] after all the wash solution has been dispensed will force air through the purification filter and dry the filter for 105 seconds. Elution solution is pneumatically driven from the eluate reservoir [49] through the purification membrane to the eluate homogenization chamber [48]. Continued application of pneumatic drive through the eluate reservoir [49] after all elution solution has been dispensed will force air through eluate homogenization chamber [48] to effect mixing by chaotic bubbling. Homogenized purified DNA solution in the eluate homogenization chamber [48] is ready for subsequent analysis.

Total nucleic acid concentration is quantified by absorbance at 260 nm. Fast PCR amplification in biochip using fluorescently-labeled primer sets specific for sexually transmitted diseases (including *Chylamdia trachomatis*, human immunodeficiency virus, *Trichomonas vaginalis*, *Neisseria gonorrhoeae*) and electrophoretic separation and detection in Genebench generate bands characteristic of the pathogen causing either symptomatic or asymptomatic infection.

While these inventions have been particularly shown and described with references to preferred embodiments thereof, it will be understood by those skilled in the art that various changes in the form and details may be made therein without departing from the spirit and scope of the inventions, as described in the appended claims.

We claim:

1. A self-contained apparatus for isolating nucleic acid from at least one unprocessed sample, said apparatus to be used with an instrument, said apparatus consisting of a macrofluidic component, a microfluidic component, at least one drive line, and two inputs, a first input for receiving the at least one unprocessed sample from a collection device, and a second input for interfacing at least one drive mechanism on said instrument at, at least one port:
   (i) said macrofluidic component consisting of: (a) at least one sample chamber, each of said at least one sample chamber composed of said first input for receiving said at least one unprocessed sample from the collection device; (b) at least one, but no less than all reagent storage chambers necessary for isolating said nucleic acid from said at least one unprocessed sample, each of said reagent storage chambers pre-filled with at least one necessary reagent, including, at least two lysis reagent storage chambers pre-filled with lysis reagent; a wash reagent storage chamber pre-filled with wash reagent; and an elution reagent storage chamber pre-filled with elution reagent;
   (ii) said microfluidic component composed of at least one microfluidic element and at least one nucleic acid purification matrix, said microfluidic component in communication with said microfluidic component via said at least one microfluidic element, and said at least one drive line;
   (iii) said second input composed of at least one drive mechanism interface port for connection to said at least one drive mechanism on said instrument configured to drive the lysis reagents pre-filled in the at least two lysis reagent storage chambers, said wash reagent, and said elution reagent sequentially through said at least one microfluidic element and said at least one nucleic acid purification matrix and back into another macrofluidic chamber,
   (iv) said at least one drive line in communication with said second input for interfacing with said at least one drive mechanism on said instrument and with said at least one microfluidic element to supply controlled flow or controlled pressure or a controlled volumetric displacement of gas or liquid to the apparatus.

2. The apparatus of claim 1, wherein said collection device and/or said at least one sample chamber is labeled with a bar code or RFID.

3. The apparatus of claim 1, wherein said at least one drive mechanism is pneumatic, mechanical, magnetic, or fluidic.

4. The apparatus of claim 1, wherein the at least one unprocessed sample is selected from the group consisting of: a nasal swab, nasopharyngeal swab, buccal swab, oral fluid swab, stool swab, tonsil swab, vaginal swab, cervical swab, blood swab, wound swab, tube containing blood, sputum, purulent material, or aspirates, a forensic swab, adhesive tape lift; an environmental air filter, water filter, and environmental swab.

5. The apparatus of claim 1, wherein the at least one nucleic acid purification matrix is selected from the group consisting of silica membranes, silica beads, silica magnetic beads, ion exchange resins, and ion exchange beads.

6. The apparatus of claim 1, wherein said at least one microfluidic element is selected from a group consisting of channels, reservoirs, active valves, passive valves, pneumatically actuated valves, reaction chambers, mixing chambers, venting elements, access holes, pumps, metering elements, mixing elements, heating elements, magnetic elements, reaction chambers, filtration elements, purification elements, drive lines and actuation lines.

7. A method for purifying nucleic acids from at least one unprocessed sample comprising,
   providing the apparatus of claim 1;
   providing the at least one unprocessed sample comprising nucleic acids to the at least one sample chamber of said apparatus;
   driving at least a portion of a first lysis reagent from a first of said at least two lysis reagent storage chambers into said at least one sample chamber to provide a first mixture;
   bubbling a gas through the first mixture to provide a stirred first mixture;
   driving at least a portion of a second lysis reagent from a second of said at least two lysis reagent storage chambers into said at least one sample chamber to provide a second mixture; and
   driving at least a portion of the stirred first mixture through said at least one nucleic acid purification matrix to provide a filtrate and a retentate, wherein the retentate comprises at least a portion of the nucleic acids;
   driving at least a portion of said wash reagent from said wash reagent storage chamber through said at least one purification matrix to provide a washed retentate and a waste;

optionally drying the washed retentate;

driving at least a portion of said elution reagent from said elution reagent storage chamber through said at least one purification matrix to provide an eluted nucleic acid solution; and bubbling a gas through the eluted nucleic acid solution to provide a homogenized eluted nucleic acid solution.

8. The method of claim 7, wherein the at least one unprocessed sample is selected from the group consisting of: a nasal swab, nasopharyngeal swab, buccal swab, oral fluid swab, stool swab, tonsil swab, vaginal swab, cervical swab, blood swab, wound swab, tube containing blood, sputum, purulent material, or aspirates, forensic swab, adhesive tape lift, adhesive tape card, environmental air filter, water filter, and an environmental swab.

9. The apparatus of claim 1, wherein the apparatus can be placed into or interfaces with another instrument that performs at least one of thermal cycling, capillary electrophoresis, microfluidic electrophoresis, nucleic acid fragment sizing, short tandem repeat (STR), Y-STR, and mini-STR, single nucleotide polymorphism, PCR, highly multiplexed PCR, Real-time-PCR, Reverse Transcription PCR, sequencing, hybridization, microarray, VNTR, immunoassays, mass spectroscopy or RFLP analyses.

10. The apparatus of claim 1, wherein a first lysis reagent storage chamber of said at least two lysis reagent storage chambers is pre-filled with guanidine and a second lysis reagent storage chamber of said at least two lysis reagent storage chambers is pre-filled with ethyl alcohol and said wash reagent storage chamber is pre-filled with an ethanol based wash reagent.

11. The apparatus of claim 1, wherein an aggregate fluid volume of the at least one sample chamber, the at least two lysis reagent storage chambers, the wash reagent storage chamber, and the elution reagent storage chamber is between about 1 and 1000 mL.

\* \* \* \* \*